United States Patent [19]
Tomioka

[11] Patent Number: 5,668,661

[45] Date of Patent: Sep. 16, 1997

[54] MICROSCOPE

[75] Inventor: Ken Tomioka, Yokohama, Japan

[73] Assignee: Nikon Corporation, Tokyo, Japan

[21] Appl. No.: 352,718

[22] Filed: Dec. 5, 1994

[30] Foreign Application Priority Data

| Dec. 7, 1993 | [JP] | Japan | 5-306503 |
| Aug. 22, 1994 | [JP] | Japan | 6-196761 |

[51] Int. Cl.⁶ .................................................. G02B 21/00
[52] U.S. Cl. ........................... 359/380; 359/368; 359/377
[58] Field of Search ........................... 359/368–390, 359/462, 466, 470, 477, 362

[56] References Cited

U.S. PATENT DOCUMENTS

| 4,657,356 | 4/1987 | Matsumura | 359/380 |
| 4,674,845 | 6/1987 | Matsumura | 359/377 |
| 4,688,907 | 8/1987 | Kleinberg | 359/377 |
| 5,227,914 | 7/1993 | Hanzawa et al. | 359/377 |
| 5,287,219 | 2/1994 | Hilderbrand et al. | 359/380 |
| 5,303,506 | 4/1994 | Weder et al. | 47/67 |

FOREIGN PATENT DOCUMENTS

| 452-822 | 10/1991 | European Pat. Off. . | |
| 2949428 | 6/1981 | Germany | 359/377 |
| 3523639 | 1/1986 | Germany . | |
| 4212924 | 1/1993 | Germany . | |
| 5-164974 | 6/1993 | Japan . | |

*Primary Examiner*—Thong Nguyen

[57] ABSTRACT

A microscope includes an objective lens and 1st, 2nd, 3rd and 4th magnification-varying optical systems of a same power, having optical axes parallel to the optical axis of the objective lens and positioned behind the objective lens and around the optical axis thereof. An objective unit houses the objective lens and the 1st, 2nd, 3rd and 4th magnification-varying optical systems. A deflection optical system directs two specified light beams, among the light beams transmitted by the 1st, 2nd, 3rd and 4th magnification-varying optical systems, to a first direction and also directs the remaining two light beams to a second direction. A first observation optical system respectively forms images, for observation, by the two light beams directed to the first direction. A second observation optical system respectively forms images, for observation, by the two light beams directed to the second direction. First and second observation units are detachably mountable alternatively to the objective unit. The first observation unit is provided with the deflection optical system and the first observation optical system, while the second observation unit is provided with the deflection optical system and the second observation optical system. The deflection optical system in the first observation unit is so constructed that the first and second directions form a predetermined first angle, and the deflection optical system in the second observation unit is so constructed that the first and second directions form a predetermined second angle different from the predetermined first angle.

15 Claims, 15 Drawing Sheets

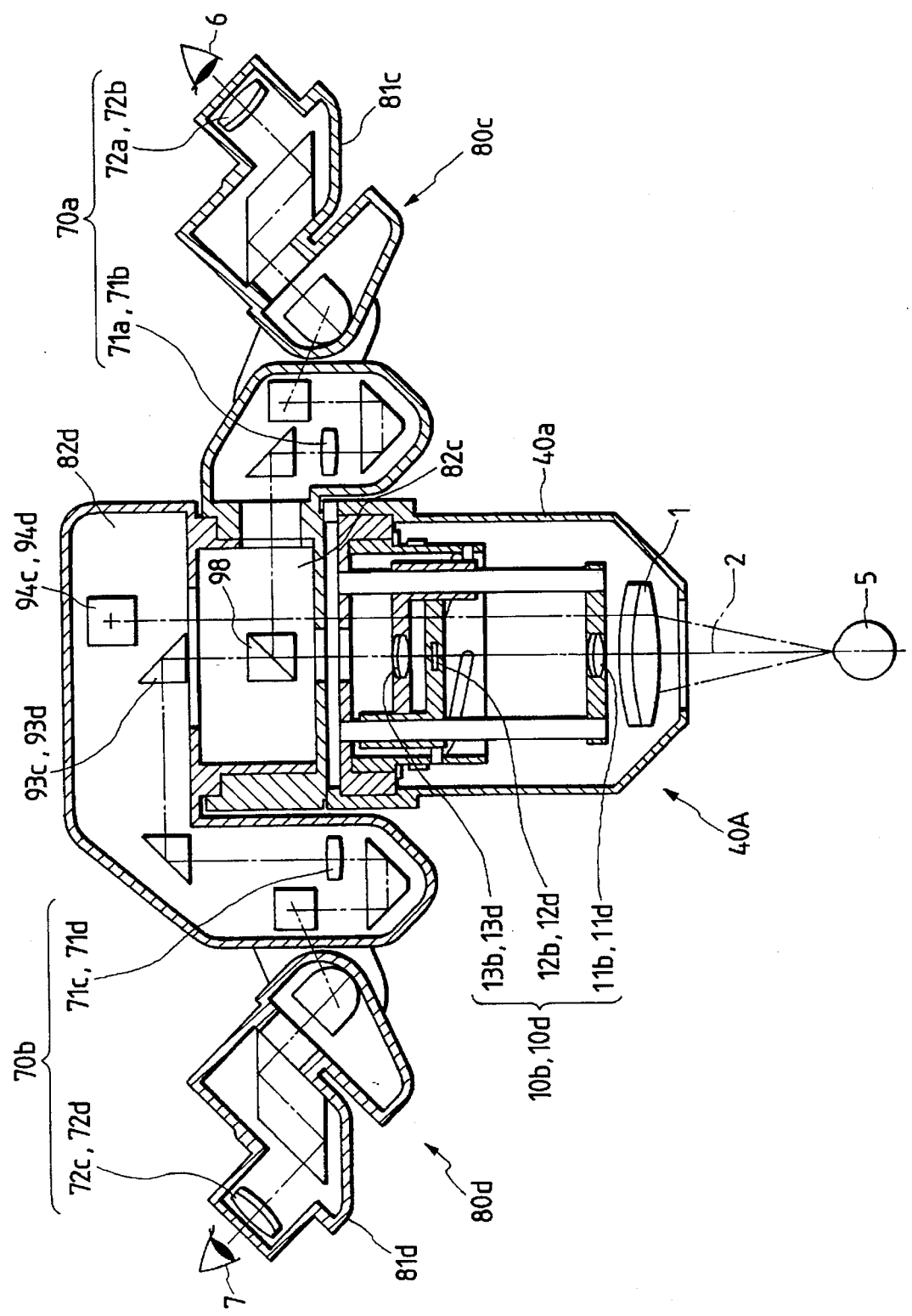

MICROSCOPE

BACKGROUND OF THE INVENTION

1. Field of the Invention

The present invention relates to a microscope for simultaneous magnified observation of an object by two persons.

2. Related Background Art

The conventional microscope for surgical operation is provided, behind an objective lens, with a pair of magnifying (zooming) optical systems positioned at right and at left, and a pair of imaging optical systems positioned likewise at right and at left, and the operator observes a magnified image of the diseased part of the patient through these optical systems.

In the surgical operation utilizing such microscope, the operator is usually assisted by an assistant, who also needs to always observe the diseased part which the operator is observing and to effect recording of the diseased part for example by photographing.

For this reason, the conventional surgical microscope of this kind is provided, for example between the magnifying optical systems and the imaging optical systems, with a pair of light beam splitting optical systems positioned at right and at left, thereby securing the light beams to be delivered to the eyes of the operator, while a light beam split by a light beam splitting optical system, for example at the left, is used for observation by the assistant and a light beam split by the other light beam splitting optical system, for example at the right, is used for recording.

However such conventional technology is associated with a drawback in that the assistant, receiving the light beam only from either one of the magnifying optical systems, is incapable of stereoscopic observation.

Also depending upon the nature of the surgical operation, it is desirable to alter the positional relationship of the operator and the assistant in various manner. The conventional technology is very inconvenient in this respect, because the imaging position for the operator and that for the assistant are mutually fixed, so that the position of the assistant relative to that of the operator has to be fixed in the surgical operation utilizing simultaneous observation of the diseased part by the operator and by the assistant.

SUMMARY OF THE INVENTION

The object of the present invention is to provide a microscope enabling simultaneous stereoscopic observation of the same object of observation by two persons.

It is also an object of the present invention to provide a microscope enabling simultaneous stereoscopic observation of the same object by two persons while allowing the positional relationship of the two persons to be altered.

The above-mentioned objects can be attained, according to the present invention, by a microscope comprising an objective lens; 1st, 2nd, 3rd and 4th magnifying optical systems of a same power, having optical axes parallel to the optical axis of said objective lens and positioned behind said objective lens and around the optical axis thereof; an objective unit including said objective lens and said 1st, 2nd, 3rd and 4th magnifying optical systems; a deflection optical system for directing two specified light beams, among the light beams respectively transmitted by said 1st, 2nd, 3rd and 4th magnifying optical systems, to a first direction while directing the remaining two light beams to a second direction; a first observation optical system for forming images for observation respectively by the two light beams directed to said first direction; a second observation optical system for forming images for observation respectively by the two light beams directed to said second direction; and first and second observation units alternatively attached detachably to said objective unit.

The above-mentioned objects can also be attained by a microscope comprising an objective lens; 1st, 2nd, 3rd and 4th magnifying optical systems of a same power, having optical axes parallel to the optical axis of said objective lens and positioned behind said objective lens and around the optical axis thereof; a deflection optical system for directing two light beams, transmitted by specified two among said 1st, 2nd, 3rd and 4th magnifying optical systems, into a first direction and also directing two light beams, among three light beams transmitted by three magnifying optical systems excluding one of said specified two magnifying optical systems, to a second direction; a first imaging optical system for respectively focusing the two light beams directed to said first direction; a second imaging optical system capable of relative rotation, about the optical axis of said objective lens, with respect to said first imaging optical system and adapted to respectively focus the two light beams directed to said second direction; a first observation optical system for observing the two light beams respectively focused by said first imaging optical system; and a second observation optical system for observing the two light beams respectively focused by said second imaging optical system.

The above-mentioned objects can furthermore be attained by a microscope comprising an objective lens; 1st, 2nd, 3rd and 4th magnifying optical systems of a same power, having optical axes parallel to the optical axis of said objective lens and positioned behind said objective lens and around the optical axis thereof; a deflection optical system for directing two light beams, transmitted by any two of said 1st, 2nd, 3rd and 4th magnifying optical systems, to a first direction and also directing two light beams, transmitted by any two of said magnifying optical systems, into a second direction; a first imaging optical system for respectively focusing the two light beams directed to said first direction; and a second imaging optical system capable of relative rotation, about the optical axis of said objective lens, with respect to said first imaging optical system and adapted to respectively focus the two light beams directed to said second direction.

In the above-explained configurations, the light beam taken in from the objective lens passes the 1st, 2nd, 3rd and 4th magnifying optical systems. The two light beams transmitted by any two of said four magnifying optical systems are focused by the first imaging optical system, while other two light beams transmitted by any two of said four magnifying optical systems are focused by the second imaging optical systems.

Consequently the person looking into the first imaging optical system and the person looking into the second imaging optical system can stereoscopically observe a same object of observation.

Also in case the optical axes of the first and second imaging optical systems are mutually angled, the positional relationship of the person looking into the first imaging optical system and the person looking into the second imaging optical system can be altered by suitably using the bodies of the imaging optical systems.

Also in case the first and second imaging optical systems are capable of mutual relative rotation, the positional relationship of the person looking into the first imaging optical system and the person looking into the second imaging optical system can be altered by rotation of either of said imaging optical systems to the other.

BRIEF DESCRIPTION OF THE DRAWINGS

FIG. 21 is a cross-sectional view of the surgical microscope of the third embodiment of the present invention, in a state of observation in mutually opposite positions in which the second stereoscopic observation unit is at a rotation angle of 180°.

DESCRIPTION OF THE PREFERRED EMBODIMENTS

Now the present invention will be clarified in detail by describing preferred embodiments thereof shown in the attached drawings.

At first there will be explained a first embodiment of the surgical microscope of the present invention, with reference to FIGS. 1 to 8.

Figure 1:
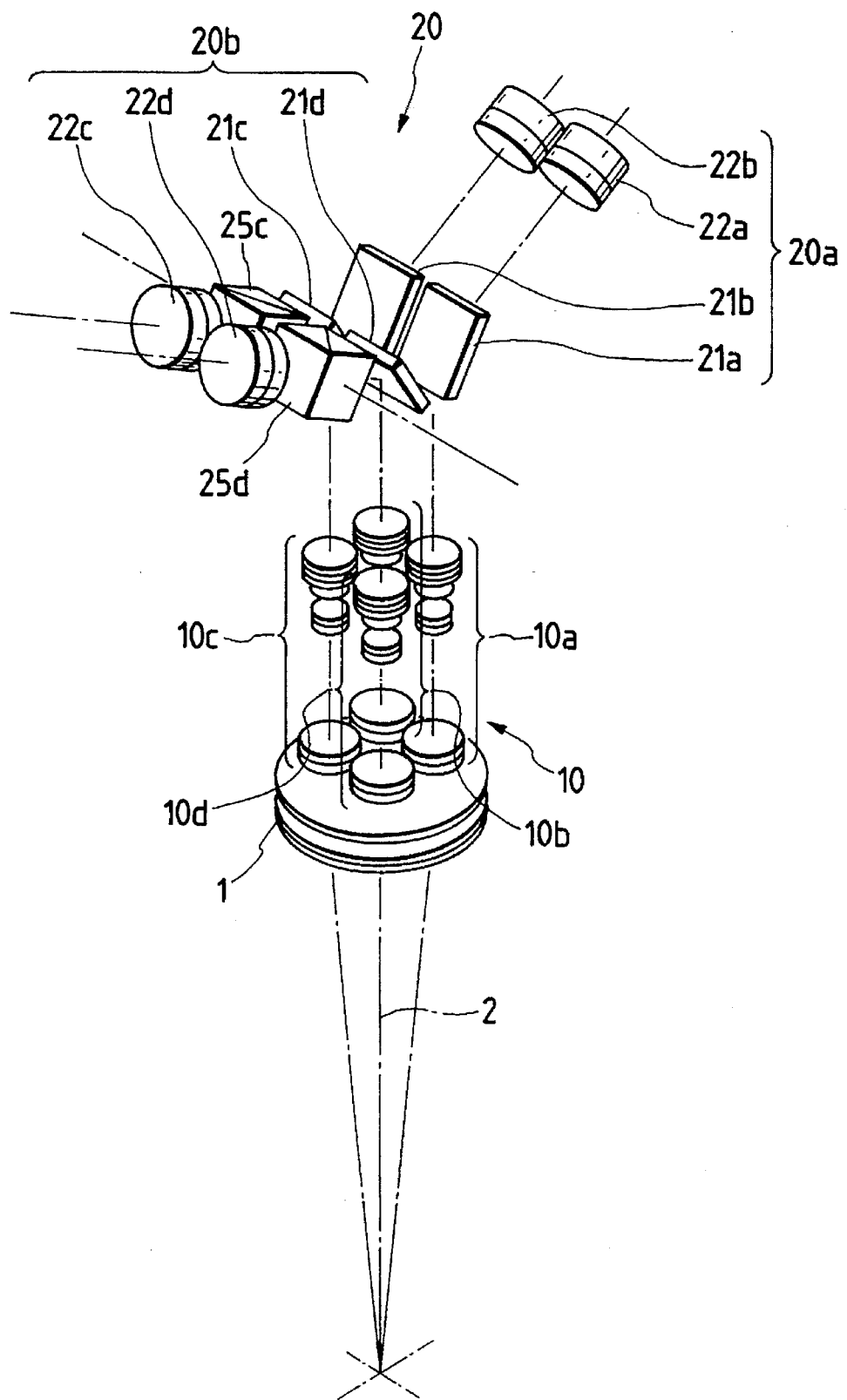
FIG. 1 is a schematic view of the configuration of the optical system of a surgical microscope, constituting a first embodiment of the present invention, in a state of observation in mutually opposed positions.

As shown in FIG. 1, the surgical microscope of the present embodiment is provided with an objective lens 1; a magnification-varying optical system 10 for varying the size of the image formed by said objective lens 1; and an observation optical system 20 including imaging lenses 22a, 22b, 22c, 22d for focusing the light beam transmitted by the magnification-varying optical system 10. The magnification-varying optical system 10 consists of 1st, 2nd, 3rd and 4th magnification-varying optical systems 10a, 10b, 10c, 10d arranged in a parallel manner mutually and in parallel to the objective lens 1, and having optical axes parallel to the optical axis 2 of said objective lens 1. The magnification-varying optical systems 10a, 10b, 10c, 10d are so positioned that the optical axes thereof are at a same distance from the optical axis 2 of the objective lens 1.

The 1st, 2nd, 3rd and 4th magnification-varying optical systems 10a, 10b, 10c, 10d are arranged in this order counterclockwise about the optical axis 2 of the objective lens 1, whereby the 1st and 3rd systems 10a, 10c are symmetrical with respect to the optical axis while the 2nd and 4th systems 10b, 10d are symmetrical with respect to the optical axis. Also they are so arranged that a line connecting the optical axes of the 1st and 3rd magnification-varying optical systems 10a, 10c perpendicularly crosses, on the optical axis of the objective lens 1, a line connecting the optical axes of the 2nd and 4th magnification-varying optical systems 10b, 10d. These magnification-varying optical systems 10a, 10b, 10c, 10d have the same refractive power.

Figure 5:
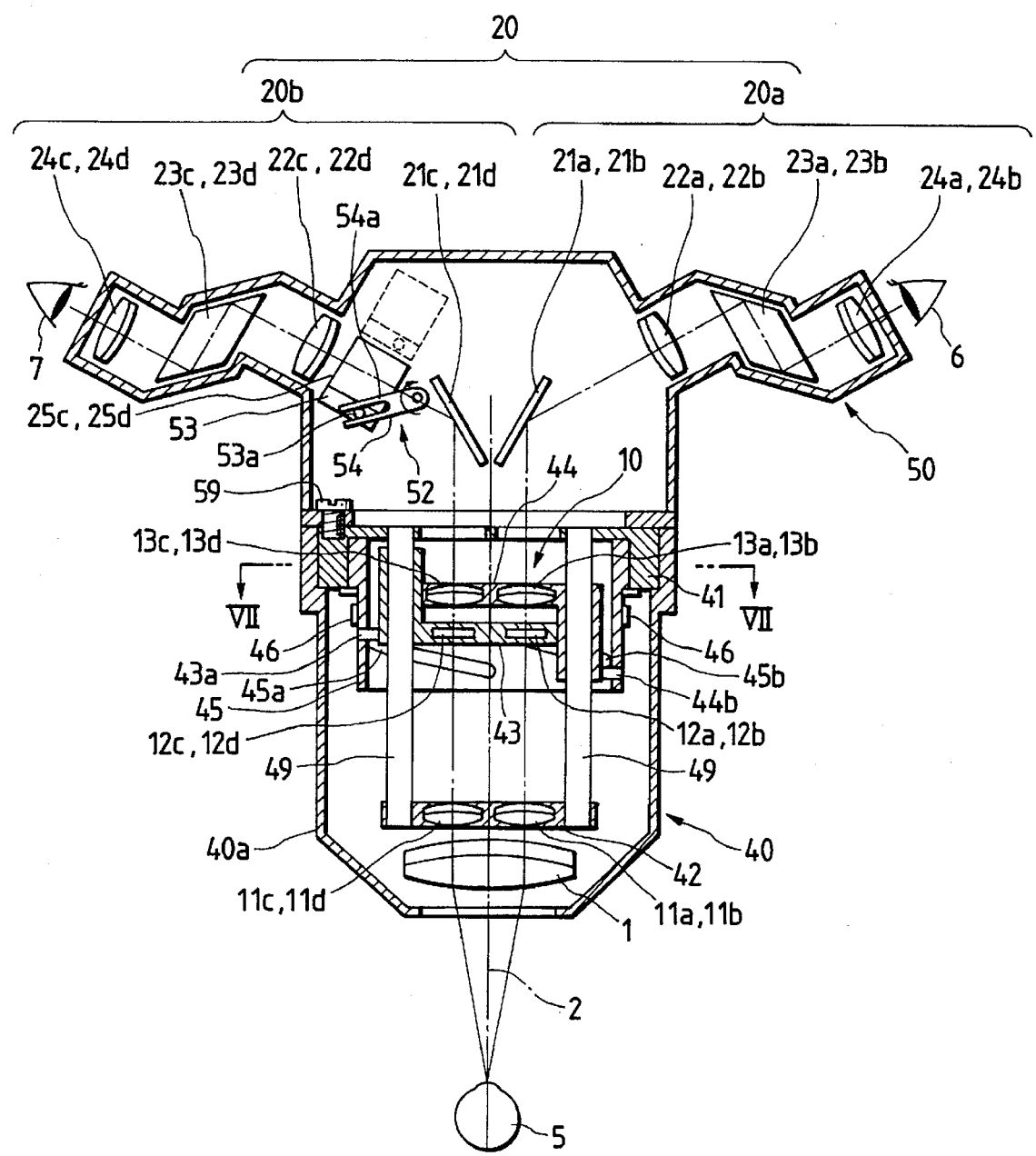
FIG. 5 is a cross-sectional view of the surgical microscope of the first embodiment of the present invention, in a state of observation in mutually opposed positions.

The magnification-varying optical systems 10a, 10b, 10c, 10d are provided, as shown in FIG. 5, with fixed lenses 11a, 11b, 11c, 11d, lower movable lenses 12a, 12b, 12c, 12d and upper movable lenses 13a, 13b, 13c, 13d. The magnification-varying optical systems 10 and the objective lens 1 are incorporated, as shown in FIG. 5, in an objective optical unit 40.

The observation optical system 20 is provided with a first observation optical system 20a (for an operator) for respectively focusing light beams transmitted by specified two of the four magnification-varying optical systems 10a, 10b, 10c, 10d, and a second observation optical system 20b (for assistant) for respectively focusing light beams transmitted by the remaining two of the four magnification-varying optical systems. In order to enable the operator 6 to stereoscopically observe a diseased part 5 as shown in FIGS. 1 and 5, the first observation optical system 20a is provided with a pair of imaging lenses 22a, 22b; a pair of rhombic prisms 23a, 23b; a pair of eyepiece lenses 24a, 24b; and a pair of totally reflecting mirrors 21a, 21b for deflecting the light beams from the magnification-varying optical systems toward the imaging lenses 22a, 22b.

Figure 2:
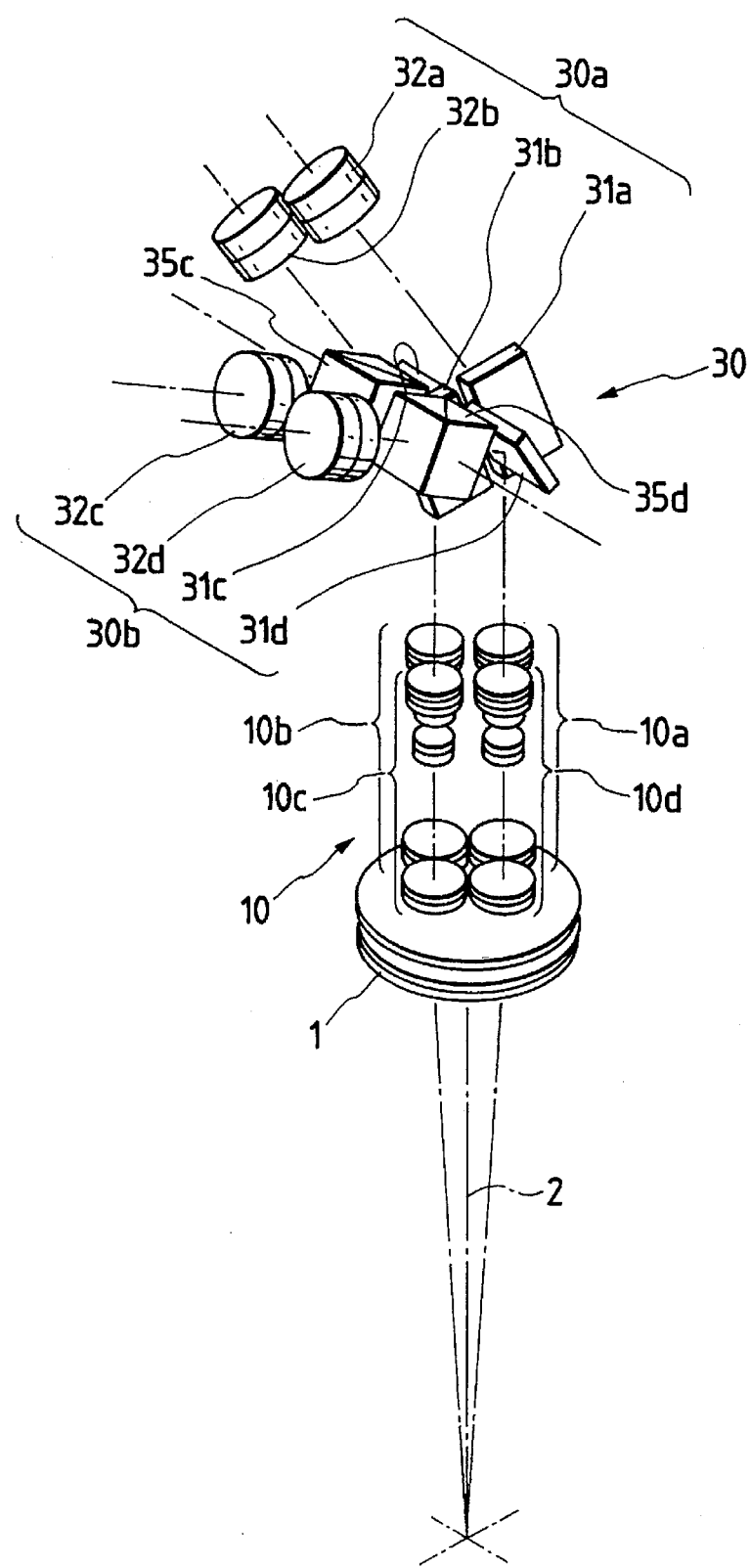
FIG. 2 is a schematic view of the configuration of the optical system of a surgical microscope, constituting the first embodiment of the present invention, in a state of observation in side-by-side positions.
Figure 6:
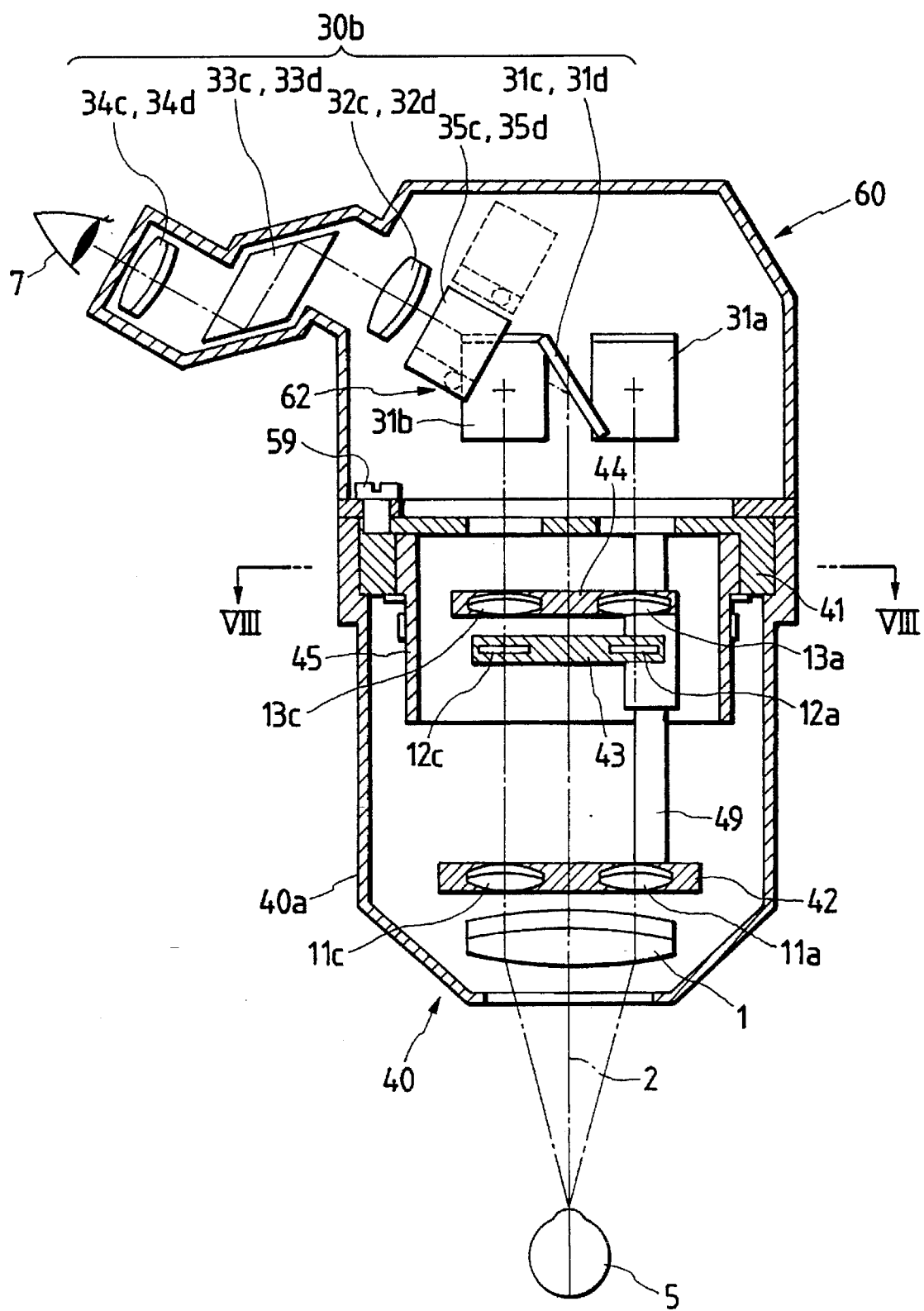
FIG. 6 is a cross-sectional view of the surgical microscope of the first embodiment of the present invention, in a state of observation in side-by-side positions.

Also in order to enable the assistant 7 to stereoscopically observe the diseased part 5, the second observation optical system 20b is provided with a pair of totally reflecting mirrors 21c, 21d; a pair of imaging lenses 22c, 22d; a pair of rhombic prisms 23c, 23d; and a pair of eyepiece lenses 24c, 24d. The observation optical system 20 is incorporated in a stereoscopic observation unit 50. For stereoscopic observation, there are provided two units; one being the above-mentioned stereoscopic observation unit 50 for observation in mutually opposite positions, in which the first and second observation optical systems 20a, 20b are so positioned, as shown in FIGS. 1 and 5, as to enable the operator 6 and the assistant 7 to observe the diseased part 5 in mutually opposite positions, while the other being a stereoscopic observation unit 60 in which first and second observation optical systems 30a, 30b are so positioned, as shown in FIGS. 2 and 6, as to enable the operator 6 and the assistant 7 to effect observation in side-by-side positions.

The objective optical unit 40 is provided, as shown in FIG. 5, with a tubular casing 40a; a fixed lens frame 42 supporting all the fixed lenses 11a, 11b, 11c, 11d of the four magnification-varying optical systems 10a, 10b, 10c, 10d; a lower movable lens frame 43 supporting all the lower movable lenses 12a, 12b, 12c, 12d of said optical systems; an upper movable lens frame 44 supporting all the upper movable lenses 13a, 13b, 13c, 13d of said optical systems; a cam tube 45 rendered rotatable about the optical axis 2 of the objective lens 1; a magnification-varying gear 48 (shown in FIGS. 7 and 8) for rotating the cam tube 45; a magnification-varying motor (not shown); guide rods 49, 49 supporting the fixed lens frame 42 in fixed manner and also supporting the movable lens frames 43, 44 movably in a direction parallel to the optical axis 2 of the objective lens 1; and a base plate 41 fixedly supporting the ends of the guide rods 49, 49 for supporting the fixed lens frame 42 and the movable lens frames 43, 44 and also rotatably supporting the cam tube 45.

The movable lens frames 43, 44 are respectively provided with cam pins 43a, 44b protruding in a direction away from the optical axis 2 of the objective lens 1. The cam tube 45 is provided thereon with cam grooves 45a, 45b which are formed spirally about the optical axis of the objective lens and adapted to engage with the cam pins 43a, 44b of the movable lens frames 43, 44. The cam tube 45 is also provided, on the external periphery thereof, with a gear 46 for meshing with the magnification-varying gear 48. The base plate is provided, in the casing 40a, rotatably about the optical axis of the objective lens 1.

In the stereoscopic observation unit 50 for observation in mutually opposite positions, the first and second observation optical systems 20a, 20b are provided in a mutually opposed relationship as shown in FIGS. 1 and 5, in order to enable the operator 6 and the assistant 7 to observe the diseased part 5 in a mutually opposed state. In addition to said optical systems 20a, 20b, the stereoscopic observation unit 50 is provided with prism-shaped beam splitters (imaging beam splitting optical systems) 25c, 25d positioned at right and at left between the paired totally reflecting mirrors 21c, 21d for the second observation optical system and the paired imaging lenses 22c, 22d for said second observation optical system 20b, and a beam splitter moving mechanism 52 for moving said beam splitters 25c, 25d. Said paired beam splitters 25c, 25d serve to distribute the light beams from the magnification-varying optical system 10 to the paired imaging lenses 22c, 22d of the second observation optical system 20b and to a television camera and a 35 mm camera.

The beam splitter moving mechanism 52 is provided with a supporting plate 53 supporting the beam splitters 25c, 25d, a rocking arm 54 for moving the beam splitters 25c, 25d together with the supporting plate 53; and a motor (not shown) for rocking the rocking arm 54. The supporting plate 53 is provided with a pin 53a, while the rocking arm 54 is provided, at the front end side thereof, with a groove 54a elongated in the longitudinal direction of the rocking arm 54 and adapted to engage with said pin 53a. A motor (not shown) is connected to the base portion of the rocking arm 54, in order to rock said arm 54 about said base portion.

The rocking arm 54 effects a rocking motion, by the function of said motor, whereby the beam splitters 25c, 25d move between a position capable of light beam distribution within the optical path of the second observation optical system 20b, and another position incapable of light beam distribution, outside said optical path.

Figure 4:
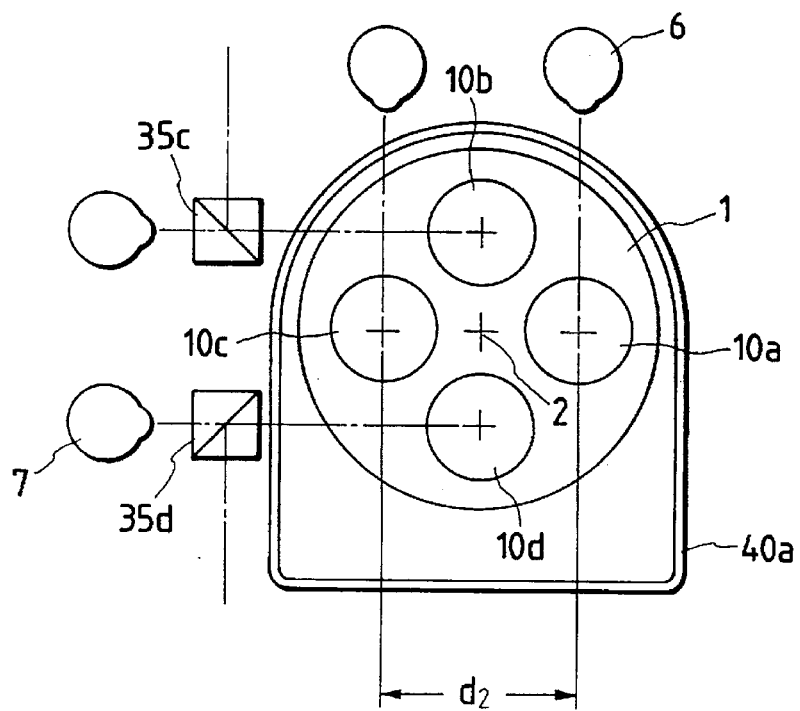
FIG. 4 is a schematic view of the configuration of the optical system of the first embodiment of the present invention, seen from the direction of the optical axis of the objective lens, in a state of observation in side-by-side positions.

In the stereoscopic observation unit 60 for observation in side-by-side positions, the first and second observation optical units 30a, 30b are so positioned that the optical axes thereof mutually form an angle of 90° as shown in FIGS. 2, 4 and 6, in order that the operator 6 and the assistant 7 can observe the diseased part 5 in positions of an angle at 90° about the optical axis 2 of the objective lens 1. As in the observation optical systems 20a, 20b in the stereoscopic observation unit 50 for observation in mutually opposite positions, the observation optical systems 30a, 30b in the unit for observation in side-by-side positions are provided with a pair of totally reflecting mirrors 31a, 31b, 31c, 31d; paired imaging lenses 32a, 32b, 32c, 32d; paired rhombic prisms 33a, 33b, 33c, 33d; and paired eyepiece lenses 34a, 34b, 34c, 34d.

The stereoscopic observation unit 60 for observation in side-by-side positions the same as the unit 50 for observation in mutually opposite positions, except for the arrangement of the observation optical systems 30a, 30b, and is further provided with prism-shaped beam splitters (imaging light beam distributing optical systems) 35c, 35d and a beam splitter moving mechanism.

Each of these units 50, 60 is detachably mountable on the objective optical unit 40, and is fixed with a screw 59 when mounted on said unit 40.

In the following there will be explained the handling of the surgical microscope of the present embodiment.

At first there will be explained, with reference to FIGS. 1, 3, 5 and 7, a case in which the operator and the assistant wish to observe the diseased part in mutually opposite positions.

Figure 3:
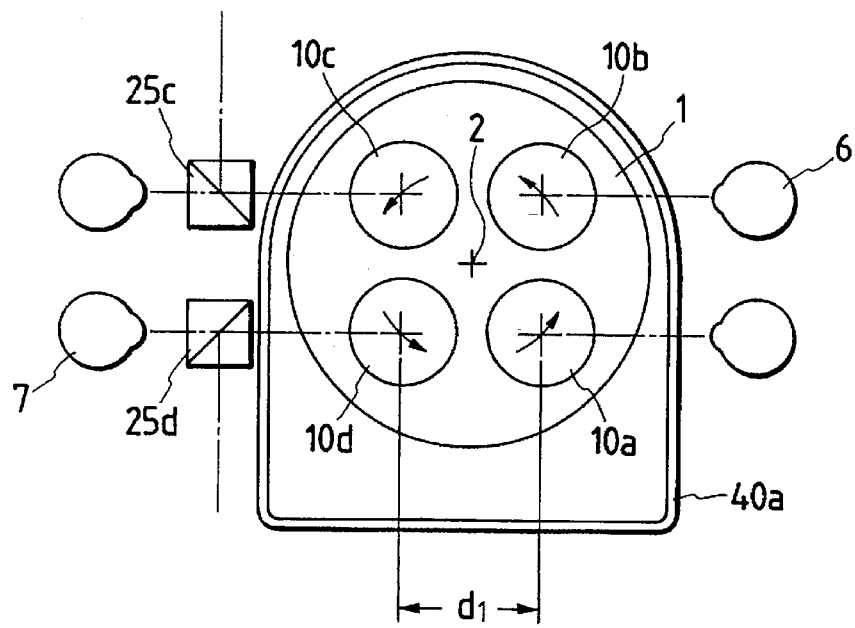
FIG. 3 is a schematic view of the configuration of the optical system of the first embodiment of the present invention, seen from the direction of the optical axis of the objective lens, in a state of observation in mutually opposed positions.
Figure 7:
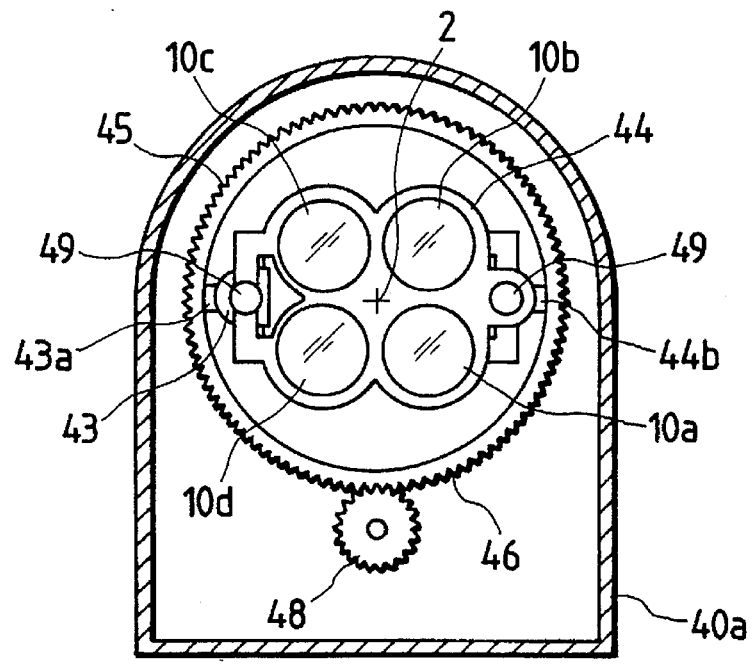
FIG. 7 is a cross-sectional view along a line VII—VII in FIG. 5.

At first the base plate 41, supporting the lens frames 42, 43, 44 of the magnification-varying optical system 10 through the guide rods 49, 49, in the casing 40a in such a manner that the rotational angle of said optical system 10 assumes a position as shown in FIGS. 3 and 7. Then the stereoscopic observation unit 50 for observation in mutually opposite positions is fixed on the objective optical unit 40 by the screw 59.

Subsequently the microscope is so set that the diseased part to be observed, for example an eye 5 of the patient, is positioned on the optical axis 2 of the objective lens 1. The operator 6 focuses the microscope on the diseased part 5 (by an unrepresented focusing mechanism), while looking into the paired eyepiece lenses 24a, 24b of the first observation optical system 20a.

The image of the diseased part is taken in from the objective lens 1, and passes the magnification-varying optical systems 10a, 10b, 10c, 10d. The light beams transmitted by the first and second magnification-varying optical systems 10a, 10b are deflected by the paired mirrors 21a, 21b of the first observation optical system 20a, then transmitted by the paired imaging lenses 22a, 22b and the paired rhombic prisms 23a, 23b of the first observation optical system 20a and form images by the paired eyepiece lenses 24a, 24b. Also the light beams transmitted by the third and fourth magnification-varying optical systems 10c, 10d are deflected by the paired mirrors 21c, 21d of the second observation optical system 20b, then transmitted by the paired beam splitters 25c, 25d, imaging lenses 22c, 22d and rhombic prisms 23c, 23d of the second observation optical system 20b and form images by the paired eyepiece lenses 24c, 24d. Consequently the diseased part 5 can be stereoscopically viewed not only by the operator 6 looking into the first observation optical system 20a but also by the assistant 7 looking into the second observation optical system 20b.

When the image of the diseased part is not distributed from the second observation optical system 20b for recording for example with a camera, the beam splitters 25c, 25d are extracted from the optical path of said optical system 20b, in order to provide the assistant 7 with a brighter and clearer image. On the other hand, in case of such recording of the image of the diseased part, the beam splitter moving mechanism 52 is activated to position the beam splitters 25c, 25d in the optical path of the second observation optical system 20b, thereby distributing the light beams from the magnification-varying optical system 10 to the assistant and to the camera.

In case of the stereoscopic observation unit 50 for observation in mutually opposite positions, the operator 6 looking into the first observation optical system 20a and the assistant 7 looking into the second observation optical system 20b are in mutually opposite positions in observing the diseased part 5, as the first and second observation optical systems 20a, 20b are provided in mutually opposed relationship as explained before.

For varying the image magnification, a magnification-varying knob (not shown) is actuated to activate a magnification-varying motor (not shown), whereby the magnification-varying gear 48 rotates the cam tube 45 about the optical axis of the objective lens 1. As a result of said rotation, the cam pins 43a, 44b of the movable lens frames 43, 44, engaging with the spiral cam grooves 45a, 45b of the cam tube 45 tend to move along said grooves.

The movable lens frames 43, 44, being limited in the moving direction by the guide rods 49, 49, do not rotate about the optical axis of the objective lens 1 but move along said optical axis 2, whereby the movable lenses 12a, 12b, 12c, 12d of the magnification-varying optical system 10 move parallel to said optical axis 2 to attain the desired magnification. The upper movable lenses 13a, 13b, 13c, 13d of the magnification-varying optical systems 10a, 10b, 10c, 10d, being fixed on the upper movable lens frame 44, move integrally. Also the lower movable lenses 12a, 12b, 12c, 12d, being fixed on the lower movable lens frame 43, move integrally. Consequently the operator 6 and the assistant 7 can observe the diseased part 5 with a same image magnification.

In the following there will be explained, with reference to FIGS. 2, 4, 6 and 8, a case where the operator 6 and the assistant 7 observe the diseased part 5 in positions of a mutual angle of 90° about the optical axis 2 of the objective lens 1.

Figure 8:
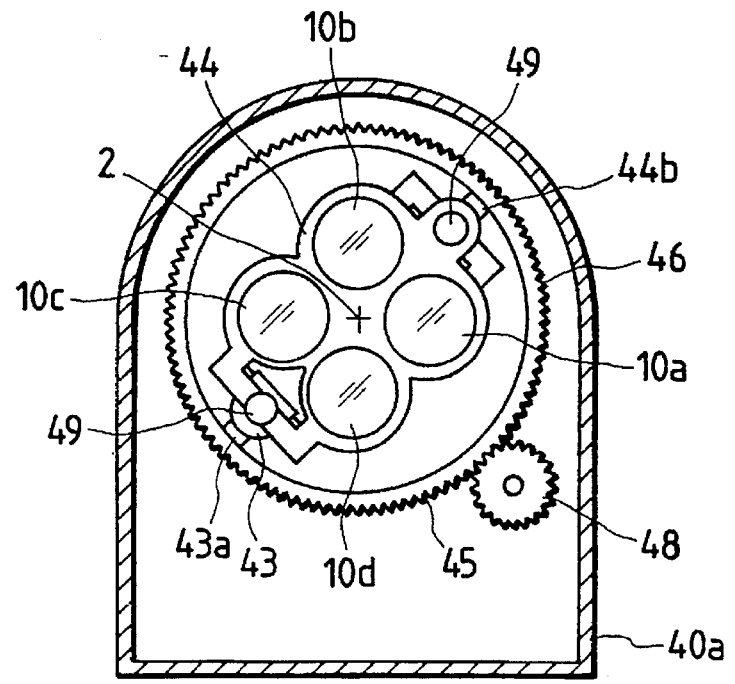
FIG. 8 is a cross-sectional view along a line VIII—VIII in FIG. 6.

At first the base plate 41, supporting the lens frames 42, 43, 44 of the magnification-varying optical system 10 through the guide rods 49, 49, is set in the casing 40a in such a manner that the magnification-varying optical system 10 assumes a rotational angle as shown in FIGS. 4 and 8 about the optical axis of the objective lens. More specifically, the base plate 41 is set with a rotation of 45° about the optical axis of the objective lens 1, from the position of the magnification-varying optical system 10 at the observation in mutually opposite positions. Then the stereoscopic observation unit 60 for observation in side-by-side positions is fixed to the objective optical unit 40 with the screw 59.

Then the microscope is so set that the diseased part 5 is positioned on the optical axis of the objective lens 1. The image of the diseased part is taken in by the objective lens 1 and passes the magnification-varying optical systems 10a, 10b, 10c, 10d. The light beams transmitted by the 2nd magnification-varying optical system 10b and the 4th magnification-varying optical system 10d, positioned diagonally thereto, are deflected by the paired mirrors 31c, 31d of the second observation optical system 30b, then transmitted by the paired beam splitters 35c, 35d, also by the paired imaging lenses 32c, 32d, rhombic prisms 33c, 33d of the second observation optical system 30b and form images by the paired eyepiece lenses 34c, 34d.

Also the light beams transmitted by the 1st magnification-varying optical system 10a and the 3rd magnification-varying optical system 10c, positioned diagonally thereto, are deflected by the paired mirrors 31a, 31b of the first observation optical system 30a, then transmitted by the paired imaging lenses 32a, 32b and rhombic prisms of the first observation optical system 30a, and form images by the paired eyepiece lenses. Consequently the diseased part 5 can be viewed stereoscopically not only by the operator 6 looking into the first observation optical system 30a but also by the assistant 7 looking into the second observation optical system 30b, who are in positions with a mutual angle of 90° about the optical axis 2 of the objective lens 1.

In case of observation of the diseased part 5 by the operator 6 and the assistant 7 positioned with a mutual angle of 90° about the optical axis 2 of the objective lens 1 without rotation of the magnification-varying optical system 10 about said optical axis, in the magnification-varying optical system 10 for observation in mutually opposite positions shown in FIG. 3, the first observation optical system 30a is given the light beams transmitted by the 2nd and 3rd magnification-varying optical systems 10b, 10c while the second observation optical system 30b is given the light beams transmitted by the 3rd and 4th magnification-varying optical systems 10c, 10d.

For this reason, the light beam transmitted by the 3rd magnification-varying optical system 10c has to be distributed to the first and second observation optical systems 30a, 30b, so that a splitting optical system such as a beam splitter is required behind said 3rd magnification-varying optical system 10c. In the present embodiment, in order to dispense with such distributing optical system, the magnification-varying optical system 10 is rotated by 45° from the state of observation in mutually opposite positions, as shown in FIG. 4, whereby the second observation optical system 30b is given the light beams transmitted by the 2nd magnification-varying optical system 10b and the 4th optical system 10d positioned diagonally thereto, while the first observation optical system 30a is given the light beams transmitted by the 1st magnification-varying optical system 10a and the 3rd optical system 10c positioned diagonally thereto.

As will be apparent from FIG. 3, the distance d1 of the optical axes of the mutually neighboring optical systems is different from distance d2 of the diagonally positioned optical systems. For this reason, it is necessary to somewhat modify the optical paths of the observation optical systems, between the opposed-position observation state (shown in FIG. 3) in which the first observation optical system 20a is given the light beams transmitted by the 1st and 2nd magnification-varying optical systems 10a, 10b and the side-by-side observation state (shown in FIG. 4) in which the first observation optical system 20a is given the light beams transmitted by the 1st optical system 10a and the 3rd optical system 10c positioned diagonally thereto.

Stated differently, the opposed-position observation state and the side-by-side observation state have to be varied not only in the directions of the optical axes of the first observation optical system 20a, 30a and the second one 20b, 30b, but also in the mutual distance of the pair of light beams introduced from the magnification-varying optical system 10. For these two reasons, the present embodiment employs two different stereoscopic observation units 50 and 60. In the present embodiment, in order to accommodate the difference in the mutual distance between the paired light beams from the magnification-varying optical system 10 between the opposed-position observation state and the side-by-side observation state, the observation optical systems 30a, 30b in the stereoscopic observation unit 60 for side-by-side observation are made somewhat different, in the deflecting directions of the mirrors and the rhombic prisms, from the observation optical systems 20a, 20b in the unit 50 for opposed-position observation.

As explained in the foregoing, the present embodiment enables stereoscopic observation of the diseased part 5 both by the operator 6 and the assistant 7, either in mutually opposite positions or in side-by-side positions. Also in the present embodiment, since the totally reflecting mirror is positioned in a position closest to the objective lens 1 in the observation optical system 20, the reaching distance RD between the eye 6 of the operator and the diseased part 5 in the vertical distance is not elongated even in case the optical path of the observation optical system is extended by the insertion of the beam splitter therein. Consequently the surgical microscope of the present embodiment enables efficient surgical operation.

As explained in the foregoing, the present embodiment can respond to a state in which the operator 6 and the assistant 7 are mutually opposed and a state in which the operator 6 and the assistant 7 are in positions of 90° about the optical axis 2 of the objective lens 1, but there may also be provided another stereoscopic observation unit for responding, for example, to a state where the operator 6 and the assistant 7 are in positions of 270° about said optical axis 2.

In the following there will be explained a second embodiment of the surgical microscope of the present invention, with reference to FIGS. 9 to 16.

Figure 9:
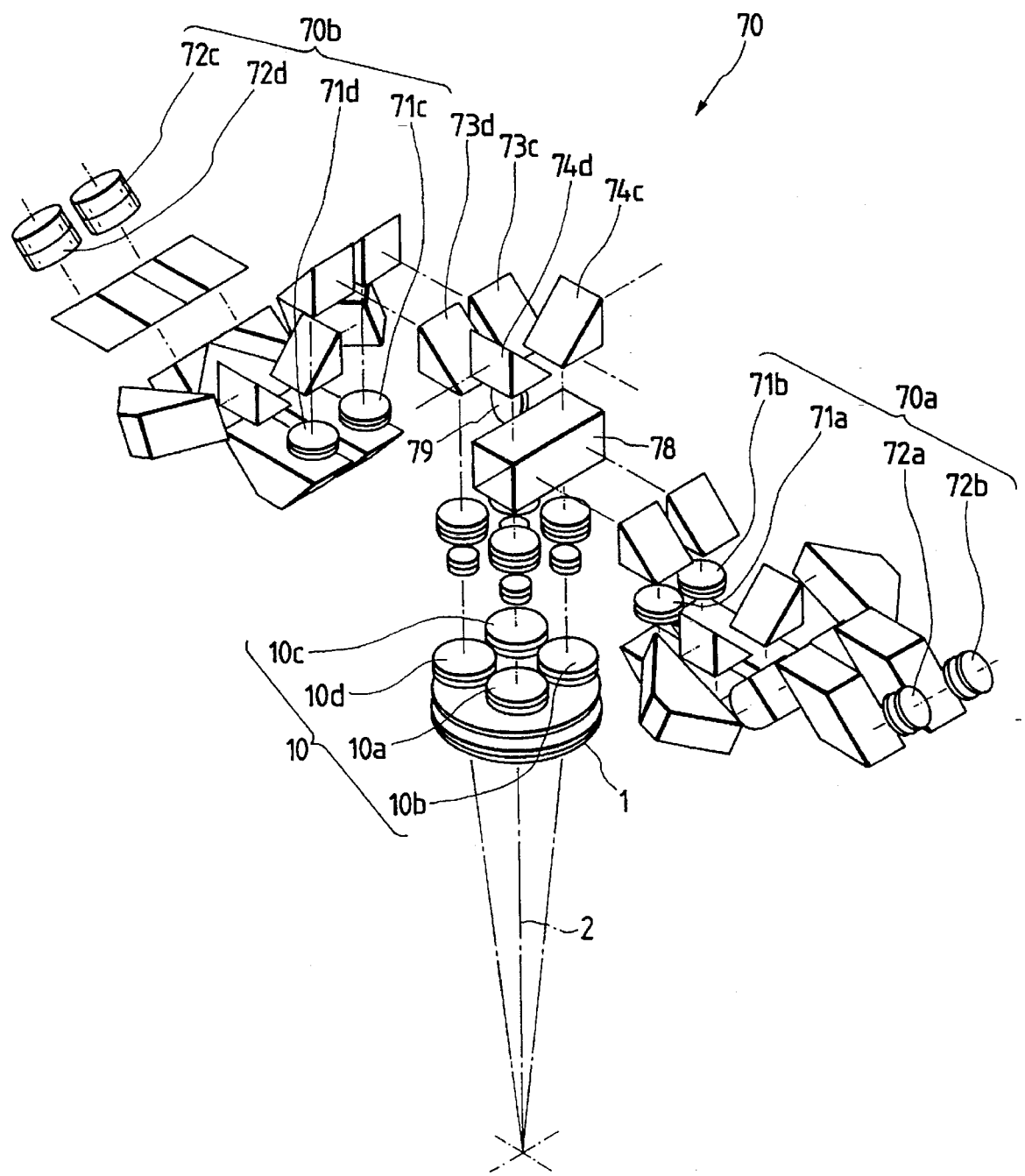
FIG. 9 is a schematic view of the configuration of the optical system of a surgical microscope, constituting a second embodiment of the present invention, in a state of observation in mutually opposite positions in which a second stereoscopic observation unit is at a rotation angle of 180°.

As shown in FIG. 9, the surgical microscope of the present embodiment is provided with an objective lens 1; a magnification-varying optical system 10 for varying the size of the image formed by the objective lens 1; and an observation optical system 70 including imaging lenses 71a, 71b, 71c, 71d for focusing the light beams transmitted by the magnification-varying optical system 10. Said optical system 10 is similar to the magnification-varying optical system in the first embodiment and is provided with 1st, 2nd, 3rd and 4th magnification-varying optical systems 10a, 10b, 10c, 10d arranged in mutually parallel manner and parallel to the objective lens 1, i.e. having optical axes parallel to the optical axis of said objective lens 1. Said optical systems 10a, 10b, 10c, 10d are arranged in such a manner that the optical axes thereof are the same distance from the optical axis 2 of the objective lens 1 and arranged in this order about said optical axis 2, whereby 1st and 3rd optical systems 10a, 10c are positioned symmetrically with respect to said optical axis while 2nd and 4th optical systems are likewise positioned symmetrically, further in such a manner that the line connecting the optical axes of the 1st and 3rd optical systems 10a, 10c rectangularly crosses, on the optical axis 2 of the objective lens 1, the line connecting the optical axes of the 2nd and 4th optical systems 10b, 10d.

Figure 13:
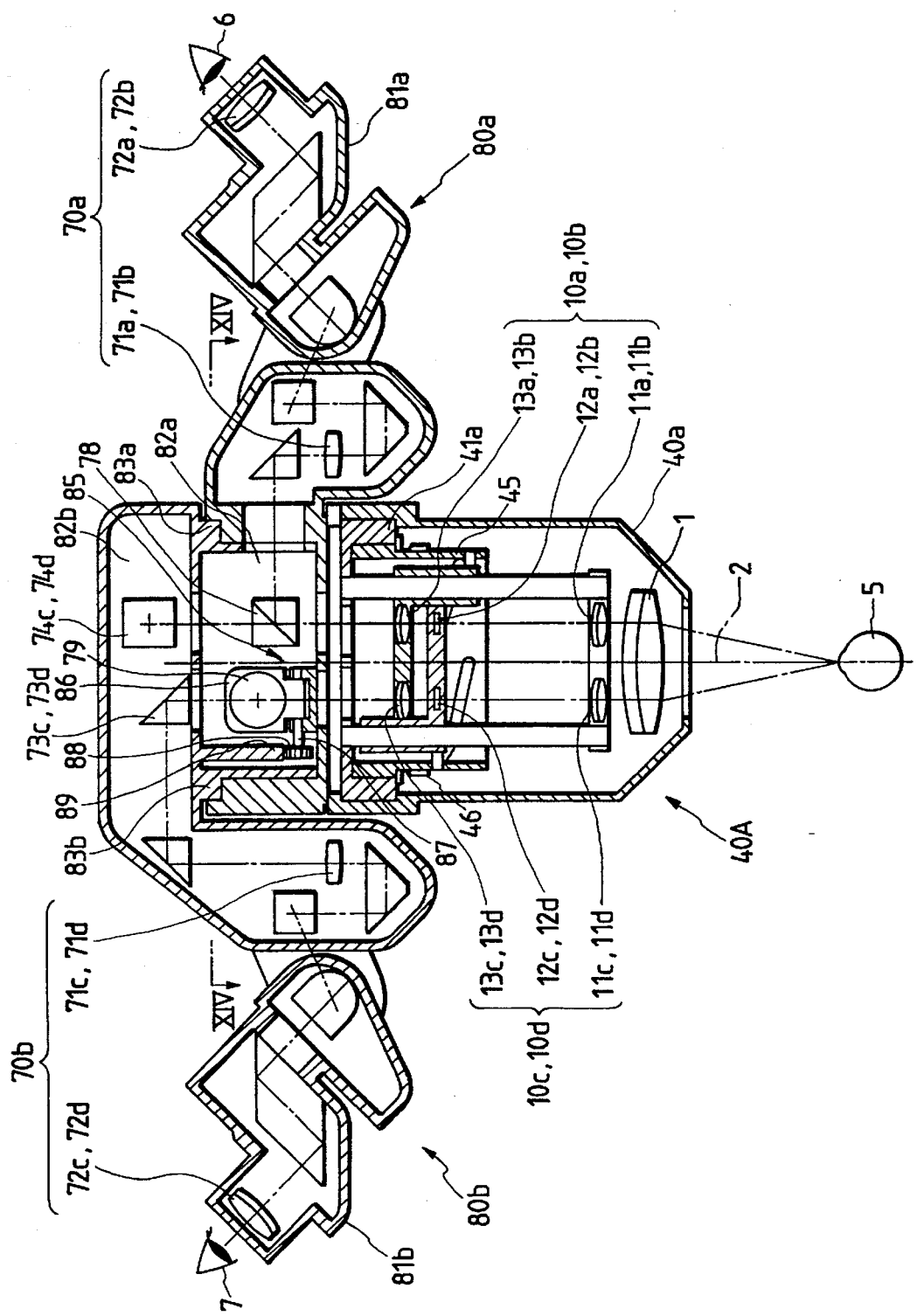
FIG. 13 is a cross-sectional view of the surgical microscope of the second embodiment of the present invention, in a state of observation in mutually opposite positions in which the second optical housing is at a rotation angle of 180°.

Above the 1st and 2nd magnification-varying optical systems 10a, 10b, there is provided a beam splitter (light beam distributing optical system) 78 for splitting the light beams transmitted by said optical systems into a first direction, perpendicular to the optical axis 2 of the objective lens 1, and a second direction, parallel to said optical axis 2. As shown in FIG. 13, the objective lens 1 and the magnification-varying optical system 10 are incorporated in an objective optical unit 40A, which is basically the same as the objective optical unit 40 in the first embodiment, except that the base plate 41a is fixed to the casing 40a so as not to rotate about the optical axis of the objective lens 1. Consequently the magnification-varying optical systems 10a, 10b, 10c, 10d are incapable of rotating about the optical axis 2 of the objective lens 1.

The observation optical system 70 is provided with a first observation optical system 70a, for the operator, for focusing the light beams transmitted by the 1st and 2nd magnification-varying optical systems 10a, 10b and directed by the beam splitter 78 into said first direction, and a second observation optical system 70b, for the assistant, for focusing two light beams, among the light beams transmitted by the 1st and 2nd magnification-varying optical systems 10a, 10b and directed by the beam splitter 78 into said second direction and the light beams transmitted by the 3rd and 4th magnification-varying optical systems 10c, 10d.

For enabling stereoscopic observation of the diseased part 5 by the operator 6, the first observation optical system 70a is provided with a pair of imaging lenses 71a, 71b; a pair of eyepiece lenses 72a, 72b; and plural pairs of optical path deflecting prisms. Said first observation optical system 70a and the beam splitter 78 are incorporated, as shown in FIG.

13, in a first stereoscopic observation unit 80a. The second observation optical system 70b is provided, for enabling stereoscopic observation of the diseased part 5 by the assistant 7, with a pair of imaging lenses 71c, 71d; a pair of eyepiece lenses 72c, 72d; and plural pairs of optical path deflecting prisms.

Said prisms include observation optical path deflecting prisms for directing specified two light beams, among the light beams transmitted by the 1st and 2nd magnification-varying optical systems 10a, 10b and directed by the beam splitter 78 into the second direction and the light beams transmitted by the 3rd and 4th magnification-varying optical systems, toward the paired eyepiece lenses 72c, 72d; and camera optical path deflecting prisms 74c, 74d for directing the remaining two light beams for example toward a camera (not shown). The second observation optical system 70b and the optical path deflecting prism are incorporated, as shown in FIG. 13, in a second stereoscopic observation unit 80b, which is rotatable, about the optical axis of the objective lens 1, with respect to the first stereoscopic observation unit 80a.

As shown in FIG. 13, the first stereoscopic observation unit 80a is provided with a casing 81a for covering the first observation optical system 70a etc.; an attenuating filter 79 for attenuating either of the light beams transmitted by the 3rd and 4th magnification-varying optical systems 10c, 10d according to the rotation angle of the second stereoscopic observation unit 80b; and a filter moving mechanism 85 for moving the attenuating filter 79. The casing 81a is provided, above the objective lens 1 (also above the magnification-varying optical system 10), with a main-axis chamber 82a which accommodates the beam splitter 78 and the attenuating filter 79 and which have apertures in the vertical direction for receiving the light beams from the magnification-varying optical system 10 and guiding the same to the second observation optical system 70b.

Above said chamber 82a there is formed a recess 83b in which the second stereoscopic observation unit 80b is rotatably mounted. The filter moving mechanism 85 is provided with a filter frame 86; a rocking shaft 87 for rocking the attenuating filter 79 together with the filter frame 86; and a rocking gear 88 provided at an end of said rocking shaft 87 for rotating said shaft 87. Said filter moving mechanism 85 moves the attenuating filter 79 either to a 3rd optical image attenuating position capable of attenuating only the light beam from the 3rd magnification-varying optical system 10c, or a 4th optical image attenuating position capable of attenuating only the light beam from the 4th magnification-varying optical system 10d, or a non-attenuating position incapable of attenuating the light beams from the magnification-varying optical systems.

The second stereoscopic observation unit 80b is provided with a casing 81b for covering the second observation optical system 70b. In said casing 81b there is formed, above the objective lens 1 (also above the main-axis chamber 82a of the first stereoscopic observation unit 80a), a main-axis chamber 82b which accommodates the observation optical path deflecting prisms 73c, 73d and the camera optical path deflecting prisms 74c, 74d and which has apertures in the bottom, for receiving the light beams transmitted by the main-axis chamber 82a of the first stereoscopic observation unit 80a. Under said chamber 82b there is formed a protruding portion 83b, which is rotatably fitted in the recess 83a of the first stereoscopic observation unit 80a. Said casing 81b also bears a filter driving gear 89, for rotating the rocking gear 88 of the first stereoscopic observation unit 80a, along with the rotation of the second stereoscopic observation unit 80b.

In the present embodiment, the beam splitter 78 and the observation optical path deflecting prisms 73c, 73d constitute an optical path deflecting system.

In the following there will be explained the handling of the surgical microscope of the present embodiment.

At first there will be explained, with reference to FIGS. 9, 11, 13 and 14, a state where the operator 6 and the assistant 7 observe the diseased part 5 in mutually opposite positions.

At first the second stereoscopic observation unit 80b is so rotated that it has a rotational angle of 180° with respect to the first unit 80a, as shown in FIGS. 9 and 13.

Figure 11:
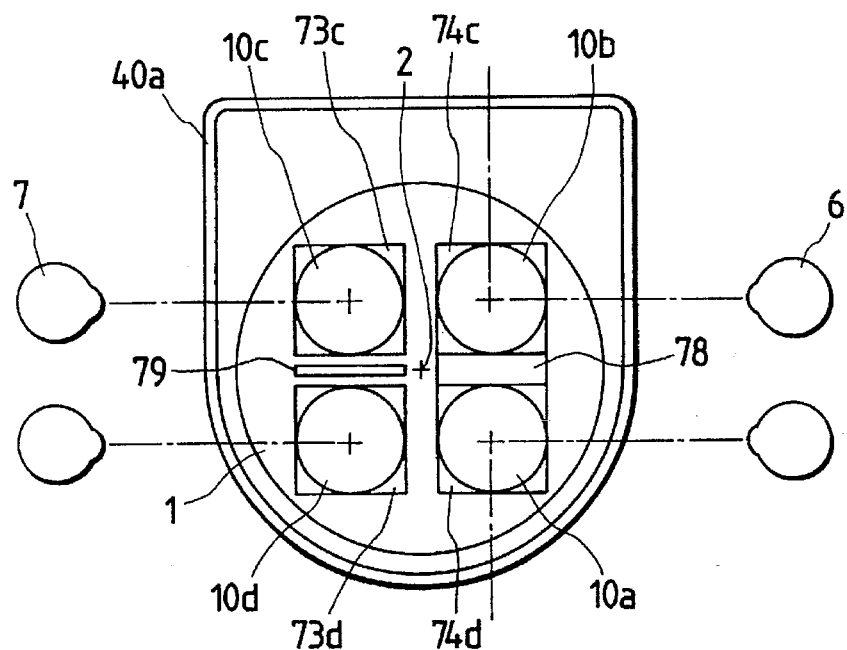
FIG. 11 is a schematic view of the optical system of the second embodiment of the present invention, seen from the direction of the optical axis of the objective lens, in a state of observation in mutually opposite positions in which the second stereoscopic observation unit is at a rotation angle of 180°.

The image of the diseased part is taken in by the objective lens 1 and passed to the magnification-varying optical systems 10a, 10b, 10c, 10d. The light beams transmitted by the 1st and 2nd magnification-varying optical systems 10a, 10b are transmitted by the beam splitter 78 as shown in FIGS. 9 and 11, and are distributed in the first direction toward the first observation optical system 70a, and in the second direction toward the camera optical path deflecting prisms 74c, 74d of the second observation optical system 70b. The light beams directed to said first direction are transmitted by the paired deflecting prisms and imaging lenses 71a, 71b of the first observation optical system 70a and form images by the paired eyepiece lenses 72a, 72b. Also the light beams directed to said second direction are deflected, by the deflecting prisms 74c, 74d of the second observation optical system 70b, toward a recording camera (not shown).

The light beams transmitted by the 3rd and 4th magnification-varying optical systems 10c, 10d are guided to the observation optical path deflecting prisms 73c, 73d of the second observation optical system 70b, then deflected therein toward the eyepiece lenses 72c, 72d thereof and form images therein.

Consequently, also in this embodiment, the diseased part 5 can be stereoscopically viewed not only by the operator 6 looking into the first observation optical system 70a but also the assistant looking into the second observation optical system 70b.

As the second stereoscopic observation unit 80b is at a rotation angle of 180° with respect to the first unit 80a about the optical axis of the objective lens 1, the operator 6 looking into the first observation optical system 70a and the assistant looking into the second system 70b are in mutually opposite positions in the observation of the diseased part 5.

Figure 14:
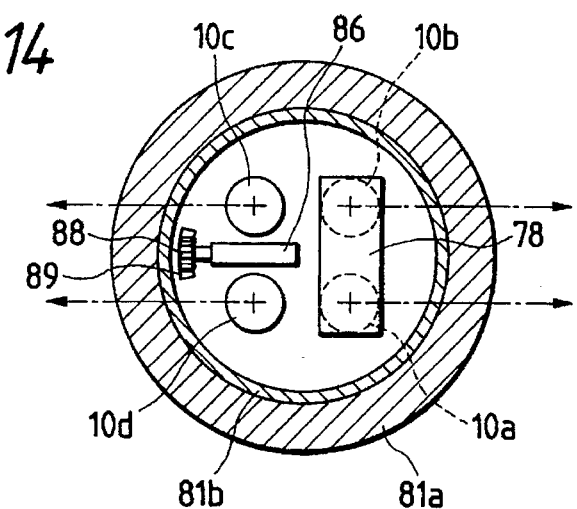
FIG. 14 is a cross-sectional view along a line XIV—XIV in FIG. 13, in a state of observation in mutually opposite positions in which the second stereoscopic observation unit is at a rotation angle of 180°.

In such opposed-position observation, the attenuating filter 79 is in the non-attenuating position as shown in FIGS. 9 and 11, so that none of 10 the light beams from the magnification-varying optical systems 10a, 10b, 10c, 10d is attenuated. Also in said state, the rocking gear 88 of the filter moving mechanism 85 meshes with the filter driving gear 89 formed on the second stereoscopic observation unit 80b as shown in FIGS. 13 and 14.

Figure 12:
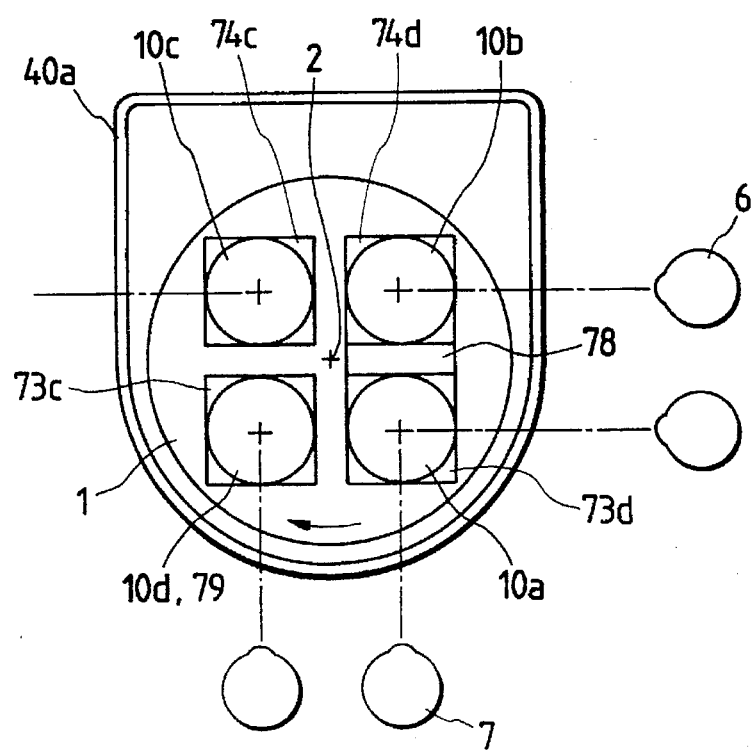
FIG. 12 is a schematic view of the optical system of the second embodiment of the present invention, seen from the direction of the optical axis of the objective lens, in a state of observation in side-by-side positions in which the second stereoscopic observation unit is at a rotation angle of 90°.
Figure 15:
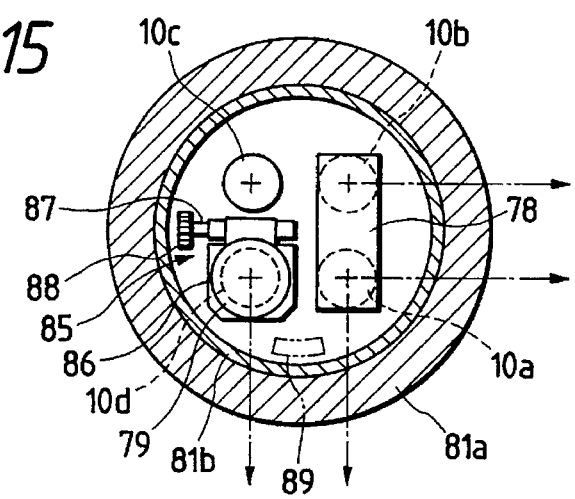
FIG. 15 is a cross-sectional view along a line XIV—XIV in FIG. 13, in a state of observation in side-by-side positions in which the second stereoscopic observation unit is at a rotation angle of 90°.

In the following there will be explained, with reference to FIGS. 10, 12 and 15, a state where the operator 6 and the assistant 7 observe the diseased part 5 in positions at an angle of 90° about the optical axis 2 of the objective lens 1.

Figure 10:
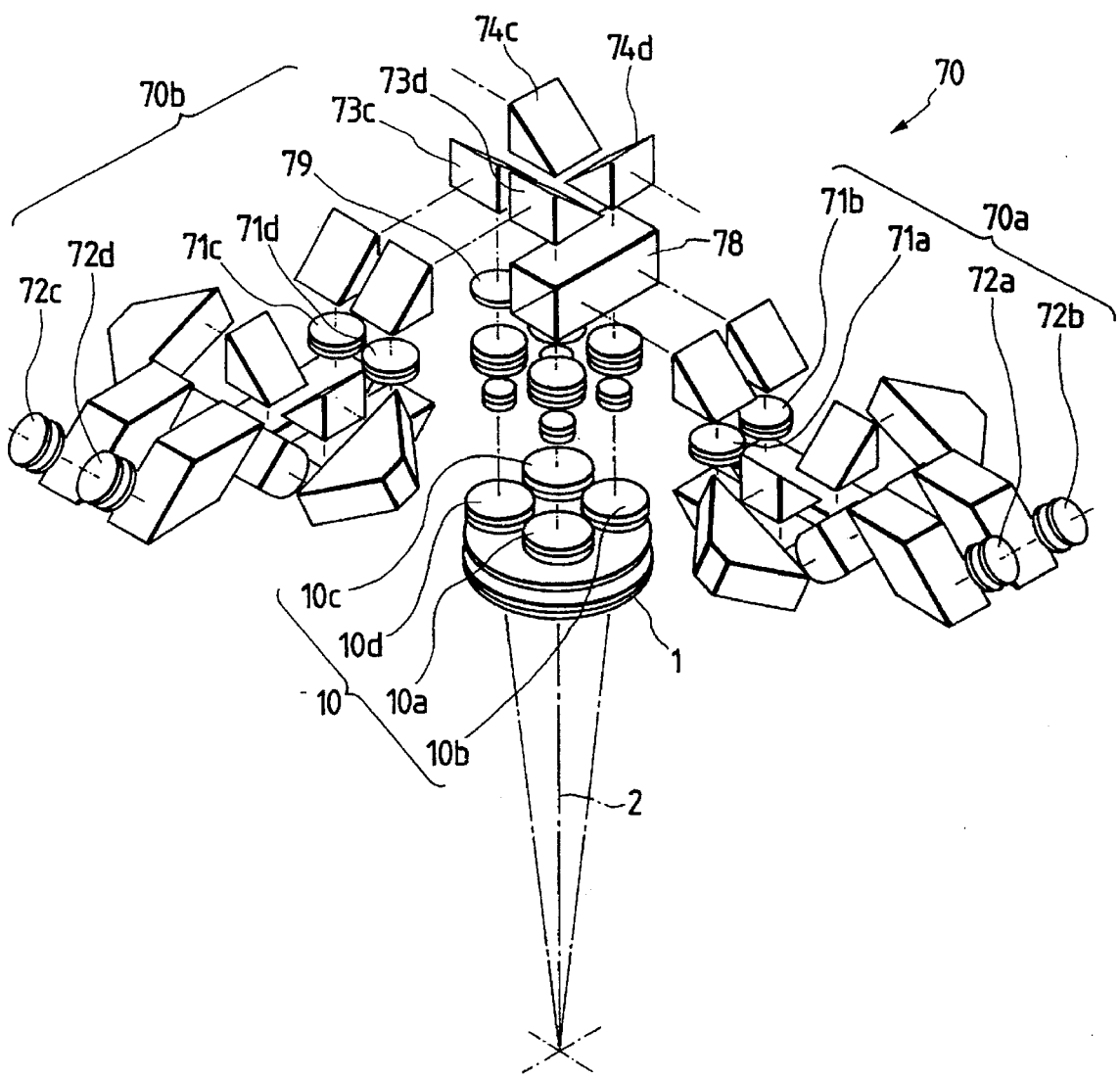
FIG. 10 is a schematic view of the configuration of the optical system of the surgical microscope, constituting the second embodiment of the present invention, in a state of observation in side-by-side positions in which the second stereoscopic observation unit is at a rotation angle of 90°.

At first the second stereoscopic observation unit 80b, including the second observation optical system 70b, is rotated, as shown in FIG. 10, to an angle of 90° to the first stereoscopic observation unit 80a including the first observation optical system 70a, about the axis of the objective lens 1.

The image of the diseased part is taken in by the objective lens 1 and passes the magnification-varying optical systems 10a, 10b, 10c, 10d. The light beams transmitted by the 1st and 2nd magnification-varying optical systems 10a, 10b are transmitted by the beam splitter 78 as shown in FIGS. 10 and 12, and are distributed into the first direction toward the first observation optical system 70a and the second direction toward the deflecting prisms 73d, 74d in the second observation optical system 70b. The light beams directed to said first direction are transmitted by the paired optical path deflecting prisms and imaging lenses 71a, 71b of the first observation optical system 70a and form images by the paired eyepiece lenses 72a, 72b.

Among the light beams directed to said second direction, the light beam from the 1st magnification-varying optical system 10a is directed to the observation optical path deflecting prism 73d of the second observation optical system 70b, then deflected therein toward the eyepiece lens 72d of the second observation optical system 70b and forms an image by the eyepiece lens 72d thereof. Also among said light beams, the light beam from the 2nd magnification-varying optical system 10b is directed to the camera optical path deflecting prism 74d of the second observation optical system 70b and deflected toward the recording camera.

The light beam transmitted by the 3rd magnification-varying optical system 10c is directly guided to the deflecting prism 74c of the second observation optical system and is deflected toward the recording camera. Also the light beam transmitted by the 4th magnification-varying optical system 10d is directed to the observation optical path deflecting prism 73c of the second observation optical system 70b and is deflected toward the eyepiece lens 72c of the second observation optical system 70b for forming an image therein.

In this manner, the light beams transmitted by the 1st and 2nd magnification-varying optical systems 10a, 10b are supplied to the first observation optical system 70a for image formation, while those transmitted by the 1st and 4th magnification-varying optical systems 10a, 10d are supplied to the second observation optical system 70b for image formation, and those transmitted by the 2nd and 3rd magnification-varying optical systems 10b, 10c are deflected toward the recording camera.

Therefore, also in a state where the operator 6 and the assistant 7 are in positions at an angle of 90° about the optical axis 2 of the objective lens 1, the diseased part 5 can be viewed stereoscopically not only by the operator 6 looking into the first observation optical system 70a but also the assistant 7 looking into the second observation optical system 70b.

In this state, the light beam from the 1st magnification-varying optical system 10a is guided, after passing the beam splitter 78, by the deflecting prism 73d of the second observation optical system 70b to the eyepiece lens 72d thereof, whereas the light beam from the 4th magnification-varying optical system 10d is guided, without passing the beam splitter 78, by the deflecting prism 73c of the second observation optical system 70b to the eyepiece lens 72c thereof. For this reason, the operator looking into the eyepiece lenses 72c, 72d of the second observation optical system 70b will observe images different in brightness between right and left, as he sees the image transmitted by the beam splitter 78 with his right eye and the image not transmitted with his left eye. In the present embodiment, the brighter image is attenuated by the filter 79 for balancing the brightnesses of both images.

In the following there will be briefly explained the function of the attenuating filter 79 and the filter moving mechanism 85. When the first and second stereoscopic observation units 80a, 80b are at a mutual angle of 180°, the rocking gear 88 of the filter moving mechanism 85 meshes with the filter driving gear 88 of the second stereoscopic observation unit 80b as shown in FIG. 14. When the second stereoscopic observation unit 80b is rotated by 90° (anticlockwise in FIG. 14) from this state to a state shown in FIG. 15 where the first and second units 80a, 80b form an angle of 90°, the filter driving gear 89 is rotated by said rotation of the second stereoscopic observation unit 80b, whereby the rocking gear 88 of the filter moving mechanism 85 is also rotated. As a result, the attenuating filter 79 moves about the rocking shaft 87 and becomes positioned on the optical axis of the 4th magnification-varying operation system 10d (4th optical image attenuating position) thereby attenuating the light beam therefrom.

Figure 16:
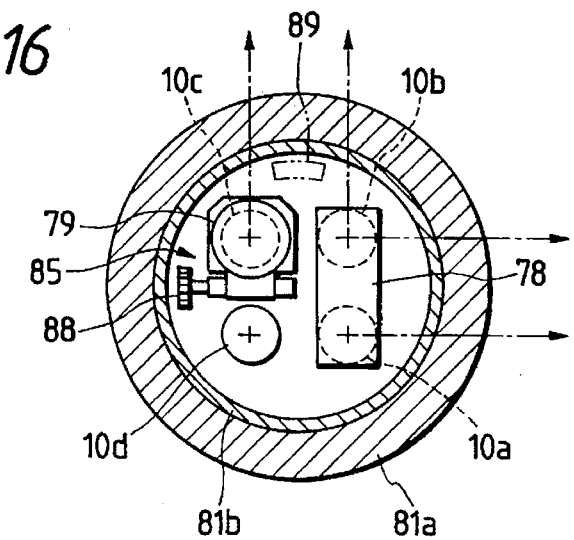
FIG. 16 is a cross-sectional view along a line XIV—XIV in FIG. 13, in a state of observation in side-by-side positions in which the second stereoscopic observation unit is at a rotation angle of 270°.

In the following there will be briefly explained, with reference to FIG. 16, a situation where the operator 6 and the assistant 7 are in directions of 270° about the axis 2 of the objective lens 1 in observing the diseased part 5.

At first the second stereoscopic observation unit 80b is rotated to a rotational angle of 270° with respect to the first Unit 80a, about the optical axis of the objective lens 1.

In this state the light beams transmitted by the 1st and 2nd magnification-varying optical systems 10a, 10b are guided to the first observation optical system 70a for image formation, while those transmitted by the 2nd and 3rd magnification-varying optical systems 10b, 10c are guided to the second observation optical system 70b for image formation, and those transmitted by the 4th and 1st optical systems 10d, 10a are deflected toward the recording camera.

Consequently, also in the situation where the operator 6 and the assistant 7 are in directions of 270° about the optical axis 2 of the objective lens 1, the diseased part 5 can be stereoscopically viewed not only by the operator 6 looking into the first observation optical system 70a but also by the assistant looking into the second system 70b.

In this state, among the light beams introduced to the second observation optical system 70b used by the assistant 7, the image from the 3rd magnification-varying optical system 10c becomes brighter than that from the 2nd optical system 10b. For avoiding this phenomenon, the attenuating filter 79 is positioned on the optical axis of said 3rd magnification-varying optical system 10c (3rd optical image attenuating position).

Thus, also in this embodiment, both the operator 6 and the assistant 7 can observe the diseased part stereoscopically even when the positional relationship of the two is altered.

In the following there will be explained a third embodiment of the surgical microscope of the present invention, with reference to FIGS. 17 to 21.

The surgical microscope of the present embodiment is basically the same as that of the second embodiment, except for differences in the arrangement of the beam splitter 78, the observation optical path deflecting prisms 73c, 73d and the camera optical path deflecting prisms 74c, 74d in said second embodiment.

In the second embodiment, the beam splitter 78 is positioned above the 1st and 2nd magnification-varying optical systems 10a, 10b for the purpose of distributing the light beams, transmitted by the 1st magnification-varying optical system 10a and the neighboring optical system 10b, into the first direction (perpendicular to the optical axis 2 of the objective lens 1) and into the second direction (parallel to said optical axis 2). On the other hand, the beam splitter 98 of the present embodiment is positioned above the 2nd and 4th magnification-varying optical systems 10b, 10d, for the purpose of distributing the light beams, transmitted by the 2nd magnification-varying optical system 10b and the diagonally positioned 4th optical system 10d, into said first and second directions. Because of the different arrangement of the beam splitter 98, the observation optical path deflecting prisms 93c, 93d and the camera optical path deflecting prisms 94c, 94d are also differently arranged in comparison with the second embodiment.

In the following the surgical microscope of this embodiment will be explained in detail. The surgical microscope of the present embodiment is provided with an objective optical unit 40A identical with that in the second embodiment; a first stereoscopic observation unit 80c is basically the same as that in the second embodiment except for the position of the beam splitter 98 incorporated therein; and a second stereoscopic observation unit 80d is basically the same as that in the second embodiment except for the positions of the observation optical path deflecting prisms 93c, 93d and the camera optical path deflecting prisms 94c, 94d incorporated therein. The first stereoscopic observation unit 80c is provided with a casing 81c, for covering a first observation optical system 70a (for the operator) which is basically the same as that in the second embodiment.

Also the second stereoscopic observation unit 80d is provided with a casing 81d for covering a second observation optical system 70d (for assistant) which is basically the same as that in the second embodiment, except for the arrangement of the observation optical path deflecting prisms 93c, 93d and of the camera optical path deflecting prisms 94c, 94d. Said second stereoscopic observation unit 80d is mounted, as in the second embodiment, on the first stereoscopic observation unit 80c rotatably with respect to the first stereoscopic observation unit 80c about the optical axis 2 of the objective lens 1 in the objective optical unit 40A.

In the main-axis chamber 82c of the casing 81c of the first stereoscopic observation unit 80c, the beam splitter 98 is provided, as already explained before, above the 2nd and 4th magnification-varying optical systems 10b, 10d. Said beam splitter 98 is fixed, as in the second embodiment, in and to the casing 81c of the first stereoscopic observation unit 80c.

Also in the main-axis chamber 82d of the casing 81d of the second stereoscopic observation unit 80d, there are provided a pair of observation optical path deflecting prisms 93c, 93d for directing the light beams, from diagonally positioned two among the four magnification-varying optical systems 10a, 10b, 10c, 10d, to the paired eyepiece lenses 72c, 72d of the second observation optical system 70d. A pair of camera optical path deflecting prisms 94c, 94d directs the light beams, from two magnification-varying optical systems (also positioned diagonally) other than those sending the light beams to said deflecting prisms 93c, 93d among the four magnification-varying optical systems 10a, 10b, 10c, 10d, for example toward a camera.

These observation optical path deflecting prisms 93c, 93d and camera optical path deflecting prisms 94c, 94d are also fixed in and to the casing 81d of the second stereoscopic observation unit 80d.

The present embodiment is not provided with the attenuating filter 79 and the filter moving mechanism 85 of the second embodiment.

In the following there will be explained the handling of the surgical microscope of the present embodiment.

Figure 19:
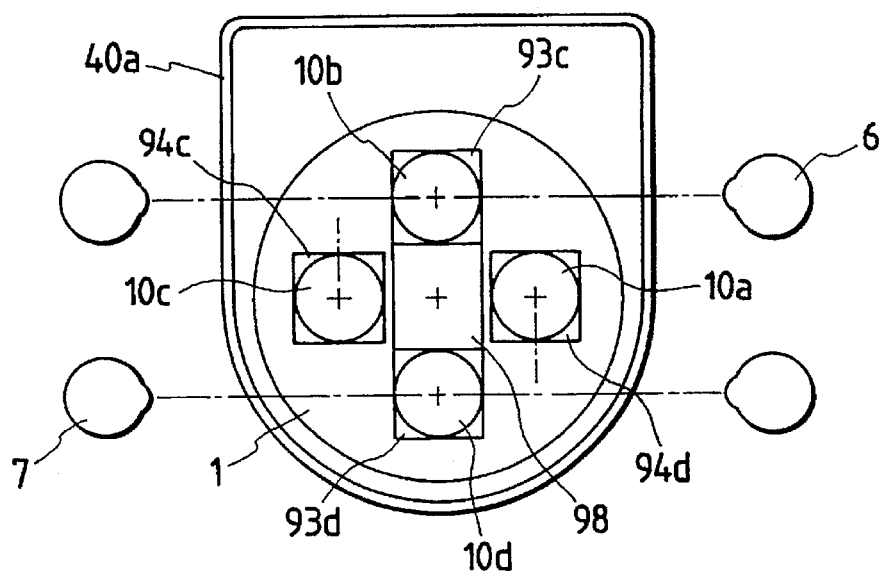
FIG. 19 is a schematic view of the optical system of the third embodiment of the present invention, seen from the direction of the optical axis of the objective lens, in a state of observation in mutually opposite positions in which the second stereoscopic observation unit is at a rotation angle of 180°.

At first there will be explained, with reference to FIGS. 17, 19 and 21, a situation where the operator 6 and the assistant 7 observe the diseased part 5 in mutually opposite positions.

Figure 17:
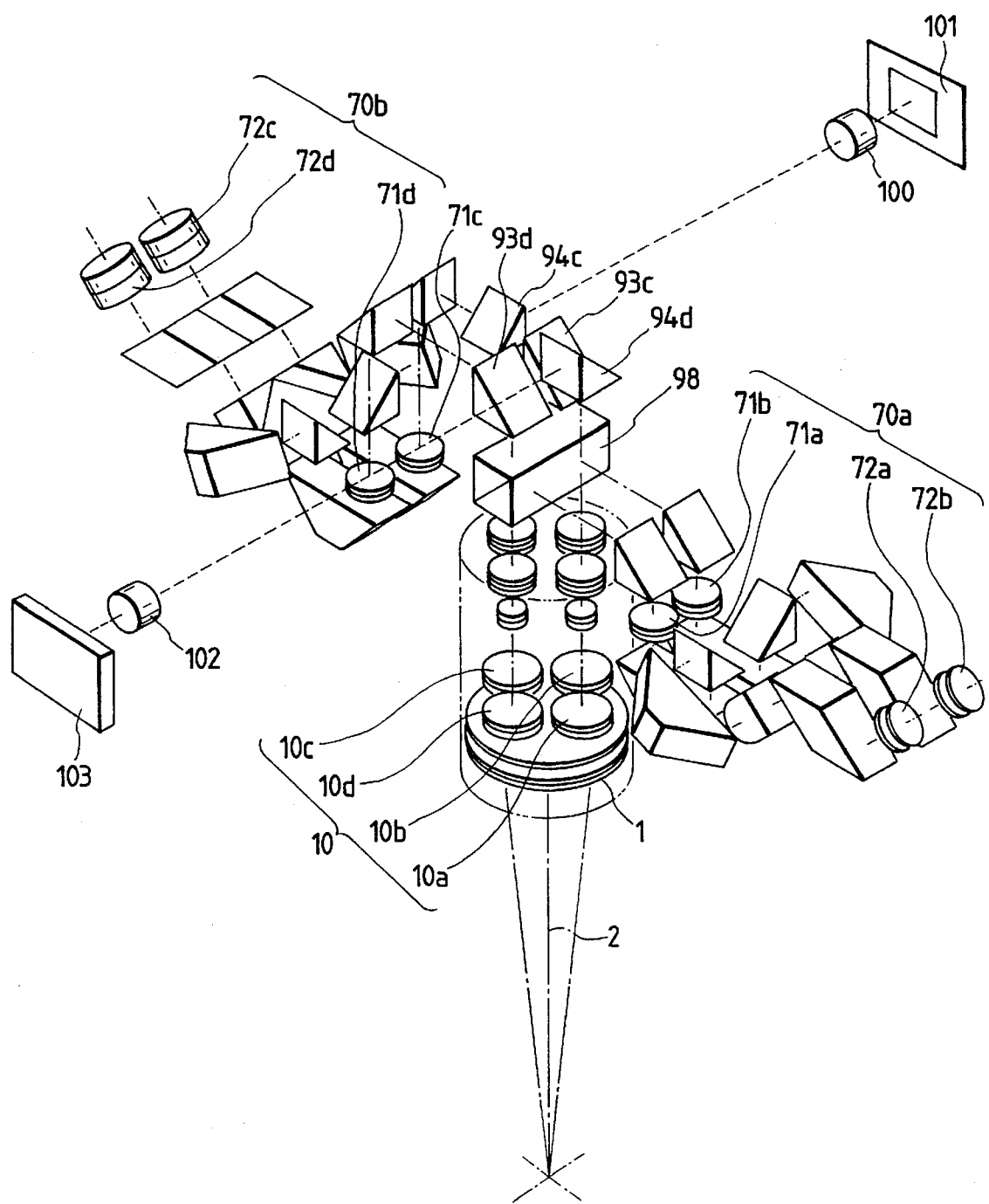
FIG. 17 is a schematic view of the configuration of the optical system of a surgical microscope, constituting a third embodiment of the present invention, in a state of observation in mutually opposed positions in which a second stereoscopic observation unit is at a rotation angle of 180°.

At first the second stereoscopic observation unit 80d is rotated to a rotational angle of 180° with respect to the first unit 80c, about the optical axis of the objective lens 1, as shown in FIGS. 17 and 21.

The image of the diseased part is taken in by the objective lens 1, and passes the magnification-varying optical systems 10a, 10b, 10c, 10d. The light beams transmitted by the 2nd and 4th magnification-varying optical systems 10b, 10d are transmitted by the beam splitter 98 as shown in FIGS. 17, 19 and 21, and are distributed in the first direction toward the first observation optical system 70a and the second direction toward the observation optical path deflecting prisms 93c, 93d of the second observation optical system 70d.

The light beams directed to said first direction are transmitted by the paired optical path deflecting prisms and imaging lenses 71a, 71b of the first observation optical system 70a and form images by the paired eyepiece lenses 72a, 72b for the operator. Also the light beams directed to said second direction are guided toward the observation optical path deflecting prisms 93c, 93d of the second observation optical system 70d, then deflected therein toward the eyepiece lenses 72c, 72d thereof, and form images therein.

Furthermore, the light beams transmitted by the 1st and 3rd magnification-varying optical systems 10a, 10c are deflected by the deflecting prisms 94c, 94d of the second observation optical system 70d toward the recording camera (not shown).

For example the light beam deflected by the prism 94c is focused by an imaging lens 100 into a film plane 101 of the camera, whereby the image of the diseased part can be photographed.

Also the light beam deflected by the prism 94d is focused by an imaging lens 102 onto a photosensor plane 103 of a CCD camera, whereby the image of the diseased part can be displayed on a monitor.

Figure 18:
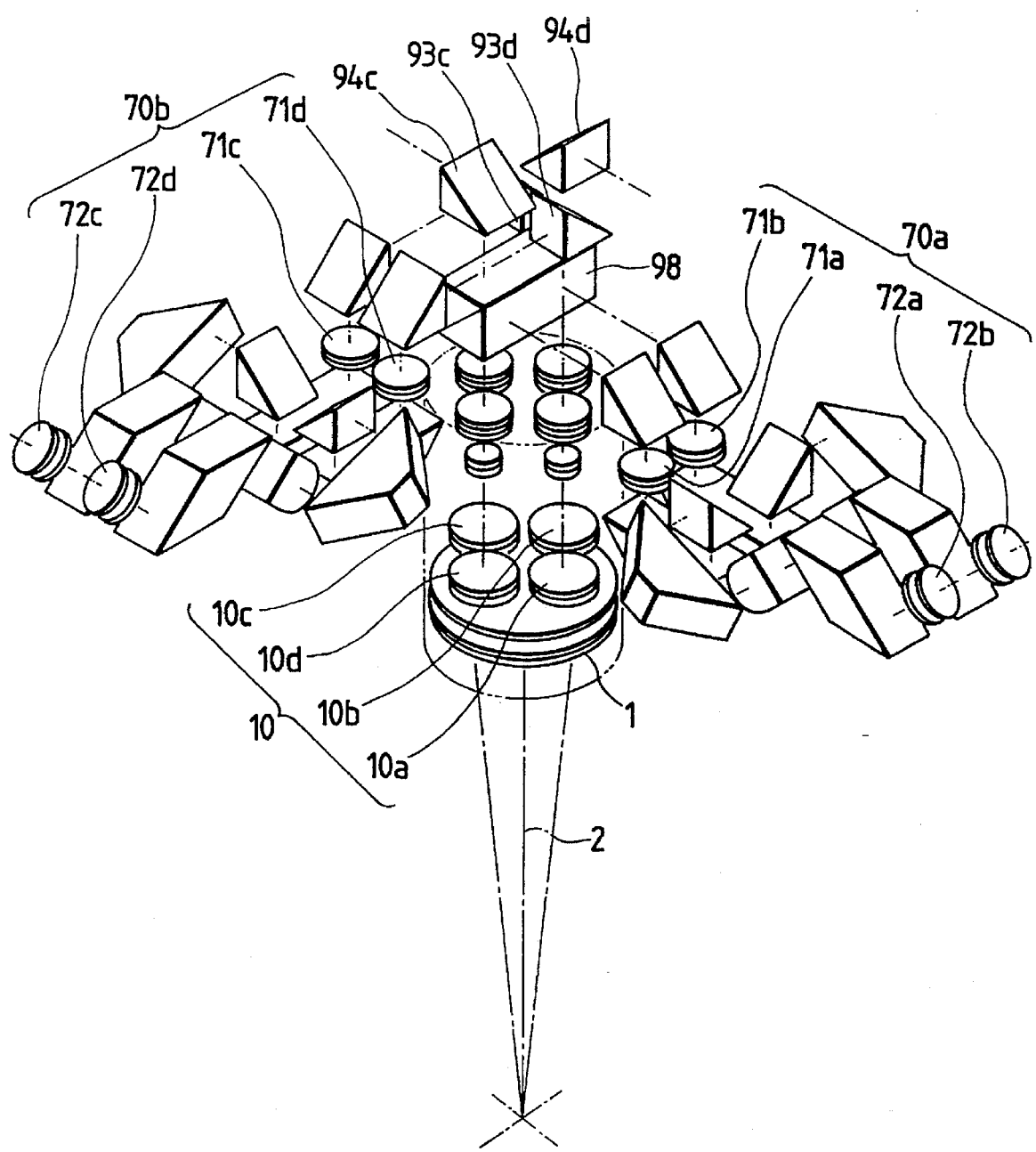
FIG. 18 is a schematic view of the configuration of the optical system of the surgical microscope, constituting the third embodiment of the present invention, in a state of observation in side-by-side position in which the second stereoscopic observation unit is at a rotation angle of 90°.
Figure 20:
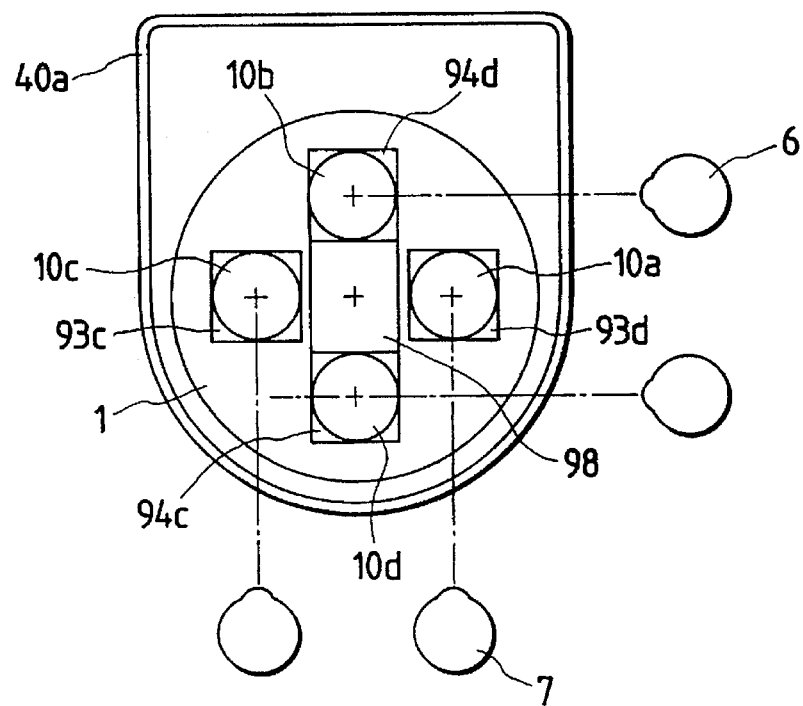
FIG. 20 is a schematic view of the optical system of the third embodiment of the present invention, seen from the direction of the optical axis of the objective lens, in a state of observation in side-by-side positions in which the second stereoscopic observation unit is at a rotation angle of 90°.

In the following there will be explained, with reference to FIGS. 18 and 20, a situation where the operator 6 and the assistant 7 observe the diseased part 5 in directions of 90° about the optical axis 2 of the objective lens 1.

At first the second stereoscopic observation unit 80d, including the second observation optical system 70d, is rotated to an angle of 90° with respect to the first stereoscopic observation unit 80c including the first observation optical system 70a, about the axis of the objective lens 1.

The image of the diseased part is taken in by the objective lens 1, and passes the magnification-varying optical systems 10a, 10b, 10c, 10d. The light beams transmitted by the 2nd and 4th magnification-varying optical systems 10b, 10d are transmitted by the beam splitter 98 as in the case where the operator 6 and the assistant 7 are in mutually opposite positions, and are distributed into the first direction toward the first observation optical system 70a and into the second direction toward the camera optical path deflecting prisms 94c, 94d of the second observation optical system 70d. The light beams directed to said first direction are transmitted by the paired deflecting prisms and imaging lenses 71a, 71b of the first observation optical system 70a and form images by the paired eyepiece lenses 72a, 72b.

Also the light beams directed to said second direction are guided to the camera optical path deflecting prisms 94c, 94d of the second observation optical system 70d and are deflected for example toward the recording camera. Also the light beams transmitted by the 1st and 3rd magnification-varying optical systems 10a, 10c are guided to the observation optical path deflecting prisms 93c, 93d of the second observation optical system 70d, then deflected therein toward the paired eyepiece lenses 72c, 72d thereof and form images therein.

As explained in the foregoing, also in this embodiment, the diseased part 5 can be viewed stereoscopically not only by the operator but also by the assistant even when the positional relationship thereof is altered, in a similar manner as in the second embodiment.

The present embodiment does not require the attenuating filter 79, in contrast to the second embodiment, because the optical paths from the objective lens 1 to the paired eyepiece lenses 72c, 72d of the second observation optical system 70b are not mutually different.

The prism-shaped beam splitters employed in the foregoing embodiments for light beam distribution may also replaced by half mirrors. Also be in the foregoing embodiments it has been assumed that the operator looks into the first observation optical system while the assistant looks into the second system, but such assumption is merely for the convenience of explanation, and the opposite mode of observation is naturally permissible.

Furthermore the foregoing embodiments have been limited to the application of the present invention to a surgical microscope, but the present invention is not limited to such application and is applicable to any microscope for magnified observation of an object by two persons, for example a teaching microscope in which a teacher and a student need to simultaneously observe the same object of observation.

What is claimed is:

1. A microscope comprising:
    an objective lens having an optical axis; 1st, 2nd, 3rd and 4th magnification-varying optical systems of a same power, having optical axes parallel to the optical axis of said objective lens and positioned behind said objective lens and around the optical axis thereof;
    a deflection optical system to direct two light beams transmitted by a specified two among said 1st, 2nd, 3rd and 4th magnification-varying optical systems, to a first direction and also to direct two light beams, among three light beams transmitted by three magnification-varying optical systems excluding either one of said specified two magnification-varying optical systems, to a second direction;
    a first imaging optical system to respectively form images using the two light beams directed to said first direction;
    a second imaging optical system provided rotatably about the optical axis of said objective lens with respect to said first imaging optical system and adapted to respectively form images by the two light beams directed to said second direction;
    a first observation optical system to observe the two light beams from said first imaging optical system; and
    a second observation optical system to observe the two light beams from said second imaging optical system.

2. A microscope according to claim 1, wherein:
    said deflection optical system includes a beam splitter; and
    said second imaging optical system includes a light attenuating filter adapted, in respectively forming images by a light beam transmitted by said beam splitter among the two light beams directed to said second direction and by a light beam transmitted by one of the two magnification-varying optical systems other than said specified two magnification-varying optical systems, to match the brightness of said light beam transmitted by the beam splitter and of said light beam transmitted by one of the two magnification-varying optical systems other than said specified two magnification-varying optical systems.

3. A microscope comprising:
    an objective lens having an optical axis; 1st, 2nd, 3rd and 4th magnification-varying optical systems of a same power, having optical axes parallel to the optical axis of said objective lens and positioned behind said objective lens and around the optical axis of said objective lens;
    a deflection optical system to direct two light beams, transmitted by any two among said 1st, 2nd, 3rd and 4th magnification-varying optical systems, to a first direction and also to direct two light beams, transmitted by any two among said 1st, 2nd, 3rd and 4th magnification-varying optical systems, to a second direction or a third direction;
    a first imaging optical system to respectively form images by the two light beams directed to said first direction; and
    a second imaging optical system provided rotatably about the optical axis of said objective lens with respect to said first imaging optical system and adapted to respectively form images by the two light beams directed to said second direction or said third direction, said deflection optical system, when the optical axes of said first and second imaging optical systems form an angle of about 90°, directing two light beams transmitted by said 1st and 2nd magnification-varying optical systems to said first direction and also directing two light beams transmitted by said 3rd and 4th magnification-varying optical systems to said second direction; and
    said deflection optical system, when the optical axes of said first and second imaging optical systems form an angle of about 180°, directing two light beams transmitted by said 1st and 2nd magnification-varying optical systems respectively to said first and third directions.

4. A microscope according to claim 3, further comprising a first eyepiece lens to observe the light beams from said first imaging optical system, and a second eyepiece lens to observe the light beams from said second imaging optical system.

5. A microscope according to claim 3, further comprising a camera adapted, when the optical axes of said first and second imaging optical systems form an angle of about 90°, to record at least one of the light beams coming from said 1st and 2nd magnification-varying optical systems through said deflection optical system, and, when the optical axes of said first and second imaging optical systems form an angle of about 180°, to record at least one of the light beams coming from said 3rd and 4th magnification-varying optical systems.

6. A microscope according to claim 3, further comprising a beam splitter to direct at least one of the light beams transmitted by said 1st, 2nd, 3rd and 4th magnification-varying optical systems to a fourth direction.

7. A microscope according to claim 6, wherein said beam splitter is provided insertably in and retractably from the optical path between said 1st and 2nd imaging optical systems and said 1st, 2nd, 3rd and 4th magnification-varing optical systems.

8. A microscope comprising:
    an objective lens having an optical axis;
    1st, 2nd, 3rd and 4th magnification-varying optical systems of a same power, having optical axes parallel to the optical axis of said objective lens and positioned behind said objective lens and around the optical axis thereof, a deflection optical system to direct two light beams transmitted by any two among said 1st, 2nd, 3rd and 4th magnification-varying optical systems, to a first direction and also to direct two light beams transmitted by any two among said 1st, 2nd, 3rd and 4th magnification-varying optical systems, to a second direction or a this direction;

a first imaging optical system to respectively form images using the two light beams directed to said first direction;

a second imaging optical system provided rotatably about the optical axis of said objective lens with respect to said first imaging optical system and adapted to respectively form images by the two light beams directed to said second direction or said third direction;

a first observation optical system to observe the two light beams from said first imaging optical system; and a second observation optical system to observe the two light beams from said second imaging optical system, said deflection optical system, when an angle formed by an optical axis of said first imaging optical system with an optical axis of said second imaging optical system is about 90°, directing two light beams transmitted by said 1st and 2nd magnification-varying optical systems, to said first direction and also directing two light beams transmitted by said 1st and 3rd magnification-varying optical systems, to said second direction, said deflection optical system, when an angle formed by the optical axis of said first imaging optical system with the optical axis of said second imaging optical system is about 180°, directing two light beams transmitted by said 1st and 2nd magnification-varying optical systems, to said first direction and also directing two light beams transmitted by said 3rd and 4th magnification-varying optical systems, to said third direction.

9. A microscope comprising:

an objective lens having an optical axis;

at least four magnification-varying optical systems, having optical axes parallel to the optical axis of said objective lens;

a deflection optical system to direct two beams transmitted by a specified two among said at least four magnification-varying optical systems, in a first direction and also to direct two beams, among three beams transmitted by three of the at least four magnification-varying optical systems excluding at least one of said specified two magnification-varying optical systems, in a second direction;

a first imaging optical system to form images using the two light beams directed in the first direction;

a second imaging optical system provided rotatably about the optical axis of said objective lens with respect to said first imaging optical system and adapted to respectively form images by the two light beams directed in the second direction;

a first observation optical system to observe the two beams from said first imaging optical system; and a second observation optical system to observe the two beams from said second imaging optical system.

10. A microscope according to claim 9, wherein:

said deflection optical system includes a beam splitter;

said beam splitter is adapted, when the optical axes of said first and second imaging optical systems form a first angle, to direct two beams transmitted by two of said at least four magnification-varying optical systems in said first direction, and also to direct two beams transmitted by another two of said four magnification-varying optical systems to said second direction; and said beam splitter is adapted, when the optical axes of said first and second imaging optical systems form a second angle, to direct two beams transmitted by said first two of said at least four magnification-varying optical systems, to said first and second directions, respectively.

11. A microscope according to claim 10, further comprising a camera adapted, when the optical axes of said first and second imaging optical systems form the first angle to record at least one of the light beams coming from two of said at least four magnification-varying optical systems through said beam splitter, and when the optical axes of said first and second imaging optical systems form the second angle, to record at least one of the light beams coming from the other of said four magnification-varying optical systems.

12. A microscope according to claim 10, further comprising a second beam splitter to direct at least one of the beams transmitted by said at least four magnification-varying optical systems in a third direction.

13. A microscope according to claim 12, wherein said second beam splitter is provided insertably in and retractably from the optical path between said first and second imaging optical systems and said at least four magnification-varying optical systems.

14. A microscope according to claim 9, further comprising a first eyepiece lens to observe the beams from said first imaging optical system, and a second eyepiece lens to observe the beams from said second imaging optical system.

15. A microscope comprising:

an objective lens having an optical axis;

a plurality of magnification-varying optical systems positioned behind said objective lens and providing at least first, second, third and fourth beams;

a first imaging optical system to form images using the first and second beams from said plurality of magnification-varying optical systems;

a second imaging optical system rotatable with respect to said first imaging optical system and adapted to form images based on the third and fourth beams or based on the second and third beams from said magnification-varying optical systems, depending upon an angle of said second imaging optical system with respect to said first imaging optical system.

* * * * *